US011052246B2

(12) United States Patent
Stewart et al.

(10) Patent No.: US 11,052,246 B2
(45) Date of Patent: Jul. 6, 2021

(54) EXPANDABLE ELEMENTS FOR DELIVERY OF ELECTRIC FIELDS

(71) Applicant: Medtronic, Inc., Minneapolis, MN (US)

(72) Inventors: Mark T. Stewart, Lino Lakes, MN (US); Brian T. Howard, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/663,301

(22) Filed: Jul. 28, 2017

(65) Prior Publication Data

US 2019/0030328 A1    Jan. 31, 2019

(51) Int. Cl.
*A61N 1/32* (2006.01)
*A61N 1/30* (2006.01)
(Continued)

(52) U.S. Cl.
CPC .......... *A61N 1/327* (2013.01); *A61B 18/1492* (2013.01); *A61N 1/303* (2013.01);
(Continued)

(58) Field of Classification Search
CPC .. A61N 1/327; A61N 1/303; A61N 1/378705; A61B 5/038; A61B 5/0006;
(Continued)

(56) References Cited

U.S. PATENT DOCUMENTS 5,454,809 A   10/1995  Janssen
6,024,740 A    2/2000  Lesh et al.
(Continued)

FOREIGN PATENT DOCUMENTS

WO   2015171921 A2   11/2015

OTHER PUBLICATIONS

Michael Kuhne, Md and Christian Sticherling, Md, Cryoballoon Ablation for Pulmonary Vein Isolation of Atrial Fibrillation: A Better Way to Complete the Circle?, The Journal of Innovation in Cardiac Rhythm Management, 2 (2011), 264-270.
(Continued)

*Primary Examiner* — Carl H Layno
*Assistant Examiner* — Roland Dinga
(74) *Attorney, Agent, or Firm* — Christopher & Weisberg, P.A.

(57) ABSTRACT

A method, system, and device for electroporation. A system may include a medical device with a plurality of electrodes borne on an expandable element and an energy generator in communication with the electrodes. The energy generator may have processing circuitry configured to selectively deliver electroporation energy to at least one of the electrodes. The processing circuitry may determine whether an alert condition is present and, if so, cease the delivery of electroporation energy to one or more electrodes identified as the cause of the alert condition and/or prevent the delivery of electroporation energy to the one or more electrodes identified as the cause of the alert condition. The energy generator may also be configured to deliver electroporation energy in a sequence of a plurality of energy delivery patterns to enhance lesion formation.

15 Claims, 13 Drawing Sheets

(51) Int. Cl.
*A61B 18/14* (2006.01)
*A61N 1/378* (2006.01)
*A61N 1/05* (2006.01)
*A61B 18/00* (2006.01)
*A61B 18/12* (2006.01)
*A61B 18/02* (2006.01)
*A61B 17/00* (2006.01)

(52) U.S. Cl.
CPC .............. *A61B 2017/00053* (2013.01); *A61B 2018/0016* (2013.01); *A61B 2018/0022* (2013.01); *A61B 2018/00214* (2013.01); *A61B 2018/00267* (2013.01); *A61B 2018/00351* (2013.01); *A61B 2018/00613* (2013.01); *A61B 2018/00654* (2013.01); *A61B 2018/00708* (2013.01); *A61B 2018/00839* (2013.01); *A61B 2018/00875* (2013.01); *A61B 2018/00898* (2013.01); *A61B 2018/0212* (2013.01); *A61B 2018/124* (2013.01); *A61B 2018/1467* (2013.01); *A61N 1/05* (2013.01); *A61N 1/3787* (2013.01)

(58) Field of Classification Search
CPC . A61B 5/6858; A61B 5/6853; A61B 18/1492; A61B 2018/0212; A61B 2018/00839; A61B 2018/00214; A61B 2018/124; A61B 2018/00898; A61B 2018/00708; A61B 2018/00654; A61B 2018/00613; A61B 2018/00351; A61B 2018/00267; A61B 2018/00875; A61B 2018/0016; A61B 2018/147; A61B 2018/0022; A61B 2017/00053

See application file for complete search history.

(56) References Cited

U.S. PATENT DOCUMENTS

| | | |
|---|---|---|
| 6,917,834 B2 | 7/2005 | Koblish et al. |
| 7,850,685 B2 | 12/2010 | Kunis et al. |
| 8,774,913 B2 | 7/2014 | Demarais et al. |
| 2011/0259638 A1* | 10/2011 | Sherrill .................... D04B 1/14 174/70 R |
| 2013/0030425 A1* | 1/2013 | Stewart .................. A61B 18/02 606/24 |
| 2013/0030430 A1* | 1/2013 | Stewart .............. A61B 18/1492 606/41 |
| 2013/0289551 A1 | 10/2013 | Condie et al. |
| 2014/0276124 A1 | 9/2014 | Cholette et al. |
| 2015/0157382 A1* | 6/2015 | Avitall .................. A61B 18/02 606/21 |
| 2016/0331459 A1* | 11/2016 | Townley .................. A61N 1/18 |
| 2017/0143201 A1 | 5/2017 | Claude et al. |

OTHER PUBLICATIONS

International Search Report and Written Opinion, dated Oct. 29, 2018, for corresponding International Application No. PCT/US2018/033788; International Filing Date: May 22, 2018, consisting of 17 pages.

* cited by examiner

EXPANDABLE ELEMENTS FOR DELIVERY OF ELECTRIC FIELDS

STATEMENT REGARDING FEDERALLY SPONSORED RESEARCH OR DEVELOPMENT n/a

TECHNICAL FIELD

The present invention relates to methods, systems, and devices for enhancing the efficiency and efficacy of ablation energy delivery and tissue mapping. In particular, the present invention relates to improved electrodes, electrode configurations, and energy delivery patterns of ablation energy.

BACKGROUND

Many individuals suffer from various cardiac issues which require treatments and interventions, including ablation. As people age, cardiac rhythm irregularity becomes an increasingly bigger problem and can sometimes result in death. One type of cardiac rhythm irregularity is atrial fibrillation, which is an irregular and often rapid heart rate that can increase the risk of stroke, heart failure, and other heart-related complications in an individual. In atrial fibrillation, the two upper chambers of the heart may beat chaotically and/or irregularly and lack coordination with the two lower chambers of the heart. The heart can beat irregularly and quiver instead of beating efficiently and effectively to move blood into the ventricles. An individual with atrial fibrillation may experience shortness of breath, weakness, and heart palpitations. Sometimes an individual with atrial fibrillation requires treatment which may include using ablation to correct this abnormality.

Ventricular tachycardia is another type of cardiac rhythm irregularity where there is a fast heart rhythm which begins with the ventricles. This condition may be caused by a malfunction in the heart's electrical system. When the heart's electrical impulses are disrupted and the electrical signals are sent too quickly, ventricular tachycardia can result and this rapid heartbeat may not give the ventricles enough time to fill with blood before the heart contracts. As a result, the heart may not be able to pump enough blood to the rest of the body. Some symptoms of ventricular tachycardia include lightheadedness, dizziness, and fainting. Ablation may be used to treat and/or manage ventricular tachycardia.

Medical procedures such as cardiac ablation using one or more energy modalities are frequently used to treat such conditions. However, complications may arise when using these procedures. For example, energy delivery may cause collateral damage to non-targeted tissue. Further, the procedure may not cause adequate lesion formation and, therefore, the underlying condition still persists. Certain energy modalities, such as electroporation, are delivered in short bursts that are less likely to cause thermal damage to non-target tissue. However, it may still be challenging to create adequate lesions, such as fully circumferential, contiguous, and/or transmural lesions, and fewer than all cells in a treated area may be irreversibly electroporated.

SUMMARY

The present invention advantageously provides a methods, systems, and devices for enhancing the efficiency and efficacy of ablation energy delivery to tissue. In one embodiment, a medical system includes a medical device configured to electroporate tissue, the medical device including an expandable element, the expandable element having a plurality of electrodes; and an energy generator in communication with the plurality of electrodes, the energy generator having processing circuitry configured to: deliver electroporation energy to the plurality of electrodes; receive data from the plurality of electrodes; determine whether an alert condition is present based on the data received from the plurality of electrodes; and at least one of cease a delivery of electroporation energy to the plurality of electrodes and prevent the delivery of electroporation energy to the plurality of electrodes when the processing circuitry determines the alert condition is present.

In one aspect of the embodiment, the data includes impedance measurements.

In one aspect of the embodiment, the plurality of electrodes is configured to be uniformly spaced when the expandable element is expanded.

In one aspect of the embodiment, each of the plurality of electrodes is configured to record at least one impedance measurement, the processing circuitry being configured to receive the at least one impedance measurement from each of the plurality of electrodes and selectively activate at least one of the plurality of electrodes based on the at least one impedance measurement received from each of the plurality of electrodes.

In one aspect of the embodiment, the system further includes a mapping system and the energy generator and processing circuitry are further configured to selectively connect each of the plurality of electrodes to the mapping system and record intracardiac electrogram signals from each of the plurality of electrodes.

In one aspect of the embodiment, the expandable element has a distal portion and a proximal portion, the plurality of electrodes being disposed on the distal portion of the expandable element.

In one aspect of the embodiment, the medical device may further include at least one electrode distal to the expandable element.

In one aspect of the embodiment, the at least one electrode distal to the expandable element is on a secondary medical device that is positionable distal to the medical device.

In one aspect of the embodiment, the medical device further includes a distal tip that extends distally beyond the expandable element, the at least one electrode distal to the expandable element being on the distal tip.

In one aspect of the embodiment, the energy generator is configured to deliver electroporation energy to the plurality of electrodes in a sequence of a plurality of energy delivery patterns.

In one aspect of the embodiment, the processing circuitry is configured to automatically switch between the plurality of energy delivery patterns such that a pulse train of electroporation energy is delivered in each of the plurality of energy delivery patterns at least once when the system is in use.

In one aspect of the embodiment, the medical device further includes a longitudinal axis, each of the plurality of electrodes having a teardrop shape that is tapered in a proximal-to-distal direction, the plurality of electrodes being radially arranged around the longitudinal axis.

In one embodiment, a medical system includes a medical device configured to electroporate an area of tissue, the medical device including: a balloon having a distal portion and a proximal portion; and a plurality of electrodes disposed on the distal portion of the balloon, each of the plurality of electrodes being configured to record impedance signals from the area of tissue and deliver electroporation energy to the area of tissue; and an energy generator in communication with the plurality of electrodes, the energy generator having processing circuitry configured to: receive impedance signals from the plurality of electrodes; identify at least one electrode of the plurality of electrodes that is in contact with the area of tissue based on impedance signals received from the plurality of electrodes; determine whether the plurality of electrodes has uniform spacing when the balloon is inflated based on impedance signals received from the plurality of electrodes; allow a delivery of electroporation energy to the plurality of electrodes when the processing circuitry determines the plurality of electrodes has uniform spacing when the balloon is inflated; and selectively deliver electroporation energy to the at least one electrode of the plurality of electrodes that the processing circuitry identifies as being in contact with the area of tissue.

In one aspect of the embodiment, the medical device further includes a longitudinal axis, each of the plurality of electrodes having a teardrop shape that is tapered in a proximal-to-distal direction, the plurality of electrodes being radially arranged around the longitudinal axis.

In one aspect of the embodiment, the medical balloon has a circumference, each of the plurality of electrodes having a circular shape and the plurality of electrodes being radially arranged around the circumference of the balloon.

In one aspect of the embodiment, the energy generator is configured to deliver electroporation energy to the plurality of electrodes in a plurality of energy delivery patterns.

In one aspect of the embodiment, the energy generator is configured to deliver bipolar electroporation energy between adjacent pairs of the plurality of electrodes to the area of tissue, the plurality of energy delivery patterns being a sequence of at least five energy delivery patterns.

In one aspect of the embodiment, the energy generator is configured to deliver monopolar electroporation energy between at least one of the plurality of electrodes and a supplemental electrode located distal to the balloon.

In one embodiment, a method for electroporating tissue includes positioning an expandable element of a medical device proximate an area of target tissue, the expandable element including a plurality of electrodes, each of the plurality of electrodes being configured to record impedance measurements; recording impedance measurements with each of the plurality of electrodes; transmitting the recorded impedance measurement to an energy generator; identifying, based on the recorded impedance measurements, at least one electrode of the plurality of electrodes that is in contact with the area of target tissue and that is a predetermined distance from at least one adjacent electrode of the plurality of electrodes; and then delivering electroporation energy to the identified at least one electrode in a sequence of energy delivery patterns by selectively one of activating and deactivating each of the at least one electrode of the plurality of electrodes.

In one aspect of the embodiment, the method further includes delivering the sequence of energy delivery patterns such that there is a delay following each energy delivery pattern in the sequence of energy delivery patterns and each energy delivery pattern in the sequence of energy delivery patterns has a duration that is at least as long as a corresponding following delay.

In one embodiment, a medical system may include: a medical device configured to electroporate a targeted area of tissue, the medical device including: an expandable element having a plurality of splines, each of the plurality of splines having a distal portion and a proximal portion, the plurality of splines being transitionable between a linear first configuration and an expanded second configuration; and a plurality of electrodes disposed on the distal portions of the plurality of splines, each of the plurality of electrodes being configured to record impedance signals from the targeted area of tissue and deliver electroporation energy to the targeted area of tissue; and an energy generator in communication with the plurality of electrodes, the energy generator having processing circuitry configured to: deliver electroporation energy to the plurality of electrodes in a sequence of a plurality of energy delivery patterns; and automatically switch between the plurality of energy delivery patterns of the sequence of the plurality of energy delivery patterns such that a pulse train of electroporation energy is delivered in each of the plurality of energy delivery patterns at least once when the system is in use.

In one aspect of the embodiment, the processing circuitry is further configured to: receive impedance signals from the plurality of electrodes; identify at least one electrode of the plurality of electrodes that is located proximate the targeted area of tissue based on the impedance signals received from the plurality of electrodes; and selectively deliver electroporation energy to the at least one electrode of the plurality of electrodes that the processing circuitry identifies as being located proximate the targeted area of tissue.

In one aspect of the embodiment, the processing circuitry is further configured to: determine whether the plurality of electrodes has uniform spacing when the plurality of splines are in the expanded second configuration based on impedance signals received from the plurality of electrodes; and allow a delivery of electroporation energy to the plurality of electrodes when the processing circuitry determines the plurality of electrodes has uniform spacing when the plurality of splines are in the expanded second configuration.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
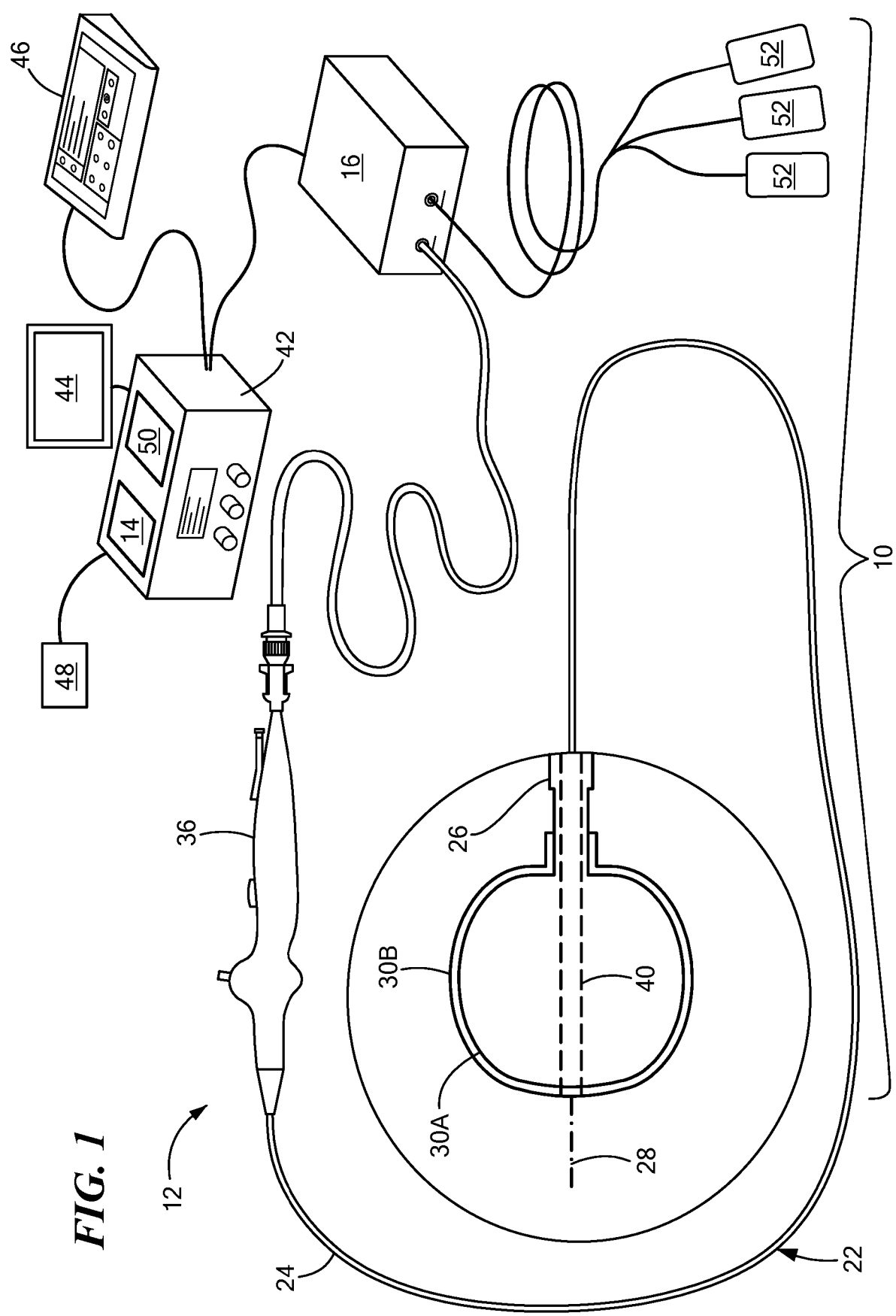
FIG. 1 shows an exemplary system including a first embodiment of a medical device for electroporating tissue.

The devices, systems, and methods disclosed herein provide for increased efficacy and efficiency of treatment procedures by enhancing lesion formation and depth, and also allow for the acquisition of enhanced mapping signals. Specifically, described herein are device and system configurations and energy delivery patterns that facilitate the irreversible electroporation of target tissue cells by delivering electrical field energy to the target tissue in a number of vectors. The devices and systems described herein enhance patient safety and increase ablation efficiency by allowing for the selective delivery of energy to individual electrodes based on electrode-tissue contact/proximity and/or proximity between electrodes.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein. For simplicity, electric fields are not shown in order to simply depict the relative polarities of monophasic or biphasic pulsed voltages or currents.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. The terms "active" or "powered" may be used to indicate electrodes that are connected to either the positive or negative polarity of the electrical energy source/energy generator, thereby producing an electric current between such powered but opposite polarity electrodes. In a similar manner, electrodes termed as "neutral," "inactive," "disconnected," "deactivated", "decoupled," or "unpowered" are those electrodes that are not connected to either of the polarities of the source of electrical energy/energy generator during such energy deliveries. In a similar manner, during energy deliveries from active electrodes, the active electrodes may be disconnected from the mapping system during the period of energy delivery and reconnected to the mapping system upon cessation of energy delivery. Additionally, following a set of deliveries of energy between active electrode pairs, the roles of active and neutral electrodes may be reversed such that the active pairs become neutral and the formerly neutral electrodes become the active electrodes, thus substantially altering the electric field vectoring between the first and second sets of energy deliveries. One having ordinary skill in the art will appreciate that multiple components may interoperate and modifications and variations are possible of achieving the electrical and data communication.

Referring now to the drawing figures in which like reference designations refer to like elements, a first exemplary embodiment of a medical system constructed in accordance with the principles of the present invention is shown in FIG. 1, generally designated as "10." The system 10 may generally include a medical device 12, such as a catheter, that may be coupled directly to an energy supply, such as an electroporation energy generator 14 including an energy control, delivering, and monitoring system, or indirectly through a device electrode distribution system 16 (which may also be referred to herein as a catheter electrode distribution system or CEDS). Further, the medical device 12 may include one or more diagnostic or treatment regions for the energetic, therapeutic, and/or investigatory interaction between the medical device 12 and a treatment site. As a non-limiting example, the treatment region(s) may include a plurality of electrodes 18 configured to deliver electroporation energy to a tissue area in proximity to the electrodes 18. Although the system is discussed herein as being used for electroporation, it will be understood that the medical device 12, generator 14, and/or other system components may additionally or alternatively be configured for use with a variety of energy modalities, including pulsed field ablation, radiofrequency (RF) ablation, laser ablation, microwave ablation, cryoablation, and the like.

The medical device 12 may serve both as a treatment device and a mapping device. The medical device 12 may include an elongate body 22 passable through a patient's vasculature and/or proximate to a tissue region for diagnosis and/or treatment. For example, the medical device 12 may be a catheter that is deliverable to the tissue region via a sheath or intravascular introducer (not shown). The elongate body 22 may define a proximal portion 24, a distal portion 26, and a longitudinal axis 28, and may further include one or more lumens disposed within the elongate body 22 thereby providing mechanical, electrical, and/or fluid communication between the elongate body proximal portion 24 and the elongate distal portion 26.

The medical device 12 may further include one or more expandable elements 30 at, coupled or affixed to, or otherwise on the elongate body distal portion 26 for energetic, therapeutic, diagnostic and/or investigatory interaction between the medical device 12 and a treatment site or region. As a non-limiting example, the device 12 may include an expandable element 30, such as a balloon as shown in FIGS. 1-3 and 521. The medical device 12 may also include a plurality of electrodes 18 on the expandable element 30. The electrodes 18 on the expandable element 30 are not shown in FIGS. 1-3 for simplicity, but are shown and described in more detail in FIGS. 5-21. The electrodes 18 may be composed of any suitable electrically conductive material(s), such as metal or metal alloys. In a non-limiting example, the plurality of electrodes 18 may be deposited or printed onto an outer surface of the expandable element 30, or may be integrated with the material of the expandable element 30. Additionally or alternatively, the plurality of electrodes 18 may be adhered to, mounted to, affixed to, or otherwise disposed on an inner surface of the expandable element 30 or on the outer surface of the expandable element 30. In one embodiment, the medical device 12 may include a first expandable element 30A located within a second expandable element 30B (for example, as shown in FIG. 1). In this configuration, one or more electrodes 18 optionally may be located within an interstitial space between the first 30A and second 30B expandable elements.

Figure 5:
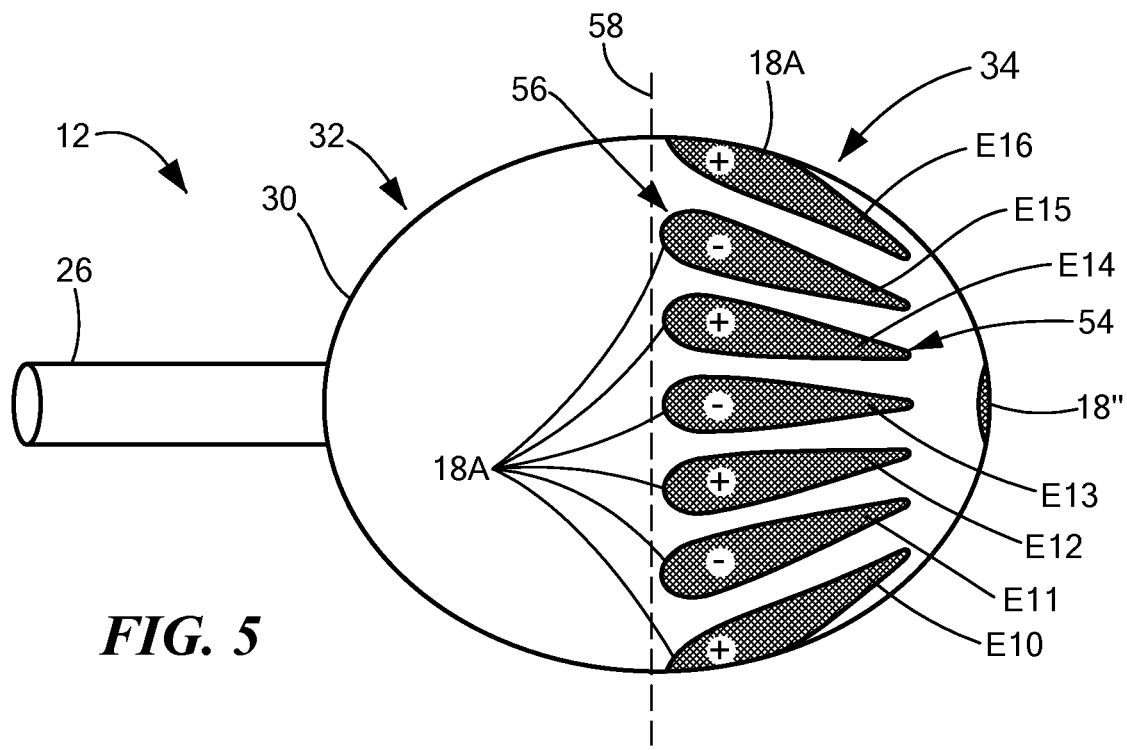
FIG. 5 shows a side view of a distal portion of a medical device having a first configuration of electrodes, the electrodes being activated in a first energy delivery pattern.

As is discussed in more detail below, the expandable element 30 may have a proximal portion 32 and a distal portion 34 (for example, as shown in FIG. 5). In one embodiment, the plurality of electrodes 18 are located on the distal portion 34 of the expandable element 30. However, it will be understood that the plurality of electrodes 18 may be additionally or alternatively located at other locations on the medical device 12, such as on the proximal portion 32 of the expandable element 30. The location of a delineation between the proximal portion 32 and the distal portion 34 of the expandable element 30 may depend on the size, shape, and configuration of the expandable element 30. In general, however, the distal portion 34 of the expandable element 30 may include at least the area of the expandable element that is configured to be in contact with an area of tissue that is oriented orthogonal to, or at least substantially orthogonal to, the elongate body longitudinal axis 28 when the medical device 12 is in use. However, at least some of the plurality of electrodes 18, or at least a portion of some of the plurality of electrodes 18, may also be located on a portion of the expandable element 30 that is not in contact with tissue when the medical device 12 is in use. Further, the expandable element 30 may be in fluid communication with a source of inflation fluid and/or cryogenic fluid (not shown) for ablation of tissue by cryoablation.

The medical device 12 may further include a handle 36 coupled to the elongate body proximal portion 24. The handle 36 may include circuitry for identification and/or use in controlling of the medical device 12 or another component of the system. Additionally, the handle 36 may also include connectors that are mateable to the generator 14 and/or the CEDS 16 to establish communication between the medical device 12 and the generator 14. The handle 36 may also include one or more actuation or control features that allow a user to control, deflect, steer, or otherwise manipulate a distal portion of the medical device 12 from the proximal portion of the medical device 12.

Figure 2:
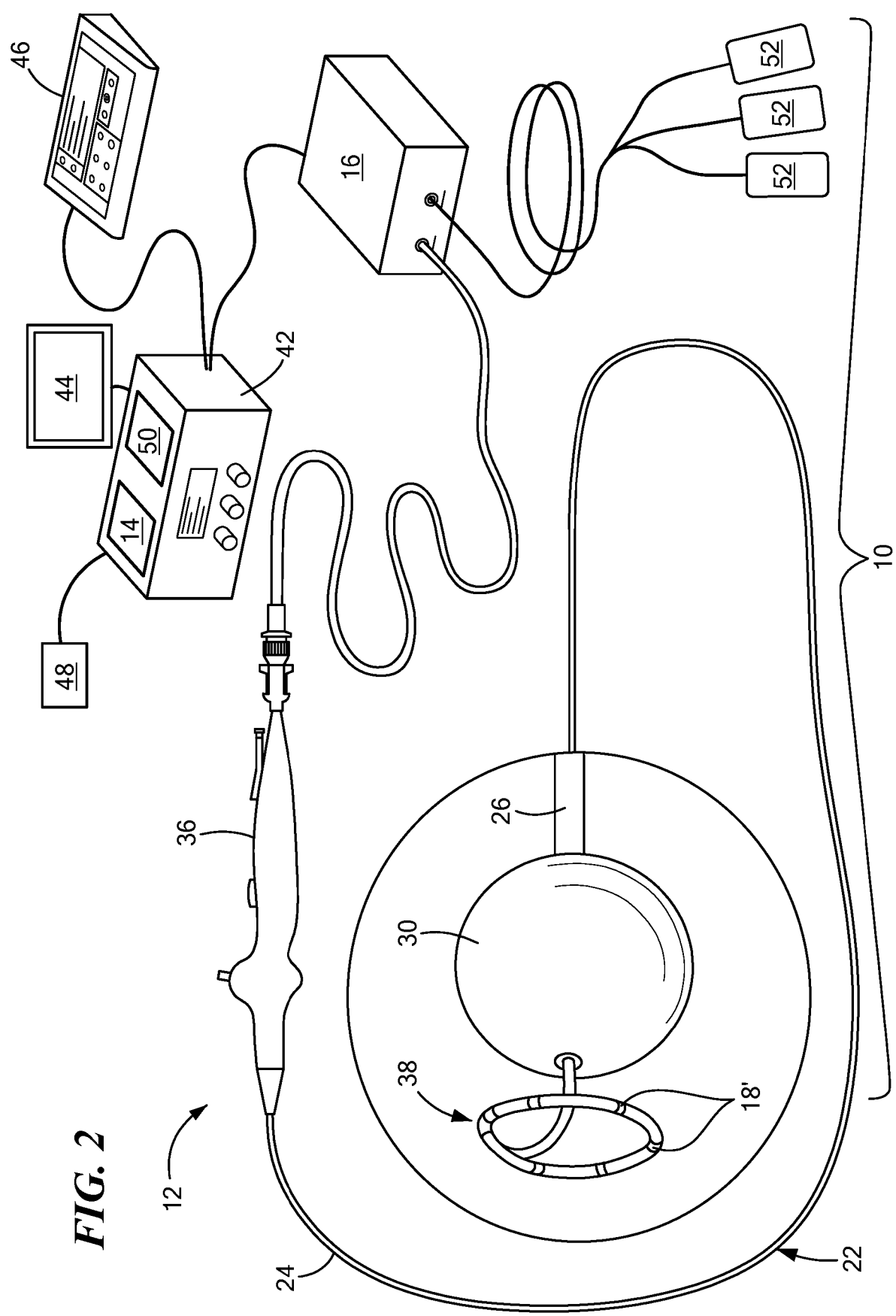
FIG. 2 shows an exemplary system including a second embodiment of a medical device for electroporating tissue.

The system 10 may further include one or more supplemental electrodes 18' located distal to the expandable element 30. In one embodiment, the one or more supplemental electrodes 18' are coupled to, affixed to, printed on, or otherwise disposed on a secondary medical device 38 that is positionable at a location distal to the expandable element 30 and electrodes 18. For example, as shown in FIG. 2, the medical device 12 may include a lumen 40, such as a guidewire lumen, that is slidably located within the elongate body 22 and extends through the expandable element 30. The secondary medical device 38 may be a guidewire including one or more supplemental electrodes 18' and may be sized and configured such that at least a portion of the secondary medical device 38 may be received within the lumen 40. Further, the secondary medical device 38 may be longitudinally movable within the lumen 40 such that at least a portion of the secondary medical device 38, such as a distal portion bearing the supplemental electrode(s) 18', may be extended out of a distal opening of the lumen 40 to position the supplemental electrode(s) 18' distal to the expandable element 30. In some modes of operation, the supplemental electrode(s) 18' of the secondary medical device 38 may be connected to the same polarity of the generator 14, thereby causing the supplemental electrode(s) 18' to operate as a single electrode, which may facilitate the creation of linear lesions between the supplemental electrode(s) 18' and the electrode(s) 18. In other modes of operation, only the secondary medical device 38 may be used to deliver electroporation energy, with some supplemental electrode(s) 18' selectively connected to a first (for example, positive) polarity of the generator 14 and other supplemental electrode(s) 18' selectively connected to a second (for example, negative) polarity of the generator 14 to deliver a variety of energy delivery patterns. The secondary medical device 38 may also be used to anchor and/or help navigate the medical device 12 and/or to map tissue.

Figure 3:
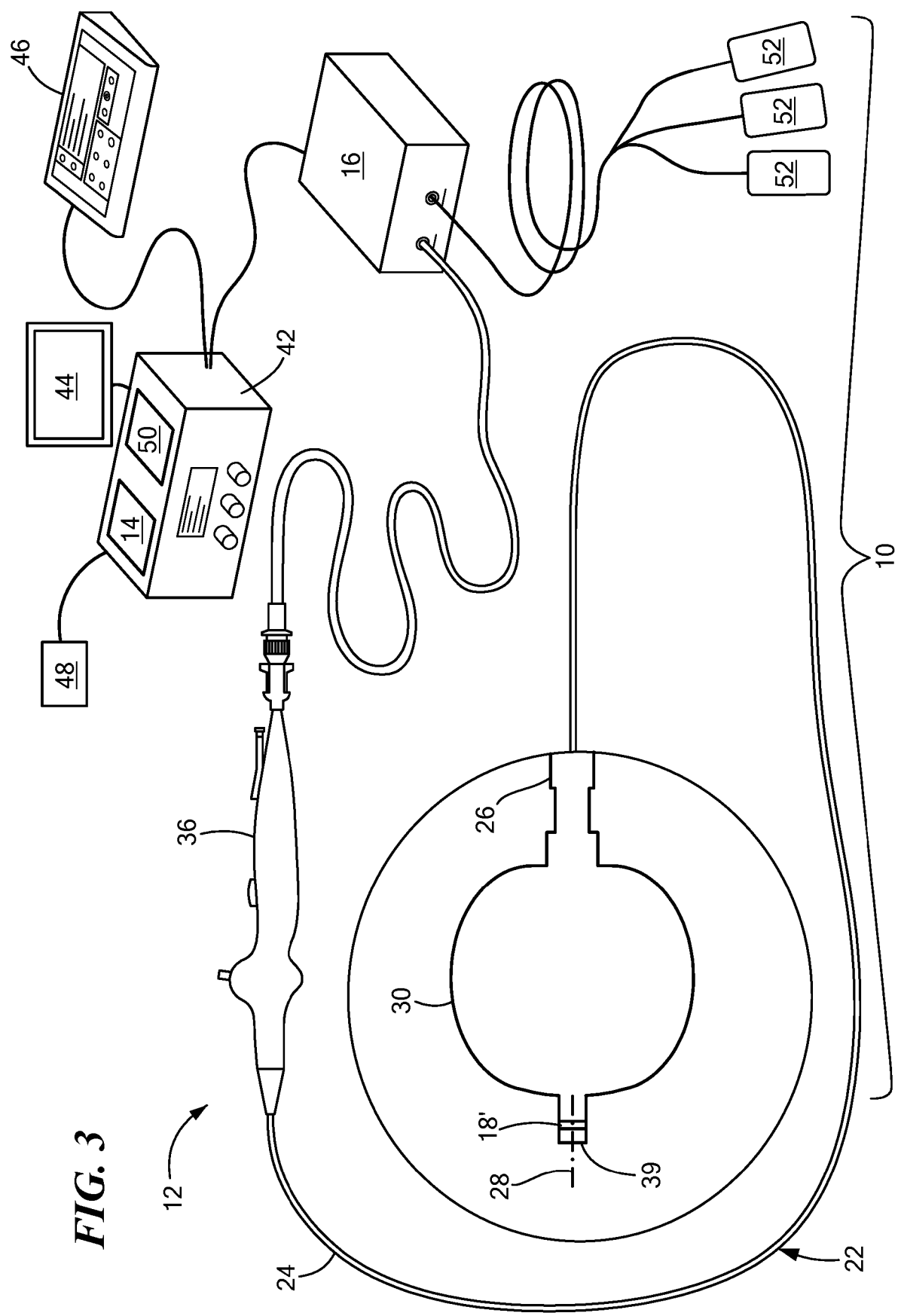
FIG. 3 shows an exemplary system including a third embodiment of a medical device for electroporating tissue.

Additionally or alternatively, the medical device 12 may include a distal tip 39 that extends distally from the distal portion 34 of the expandable element 30. The distal tip 39 may include one or more supplemental electrodes 18' (for example, as shown in FIG. 3). In another embodiment, the one or more supplemental electrodes 18' may be located on a secondary device that is separate from the medical device 12 and positionable at a location that is proximate the position of the medical device 12 (not shown). For example, the medical device 12 may be located within the left atrium proximate a pulmonary vein, whereas the secondary device is located in the pericardial space proximate the medical device 12. In another embodiment, the medical device 12 may include a distal electrode 18" on the distalmost portion of the expandable element 30 (for example, as shown in FIGS. 5-10). All electrodes of the system (including electrodes 18 on the medical device 12 and any supplemental electrodes 18') may be in electrical communication with the generator 14. Thus, energy may be delivered between one or more of the electrodes 18 on the expandable element and one or more supplemental electrodes 18' to create different ablation patterns, such as ablation patterns that are linear or extended in a proximal-to-distal direction instead of or in addition to circumferential ablation patterns.

Figure 4:
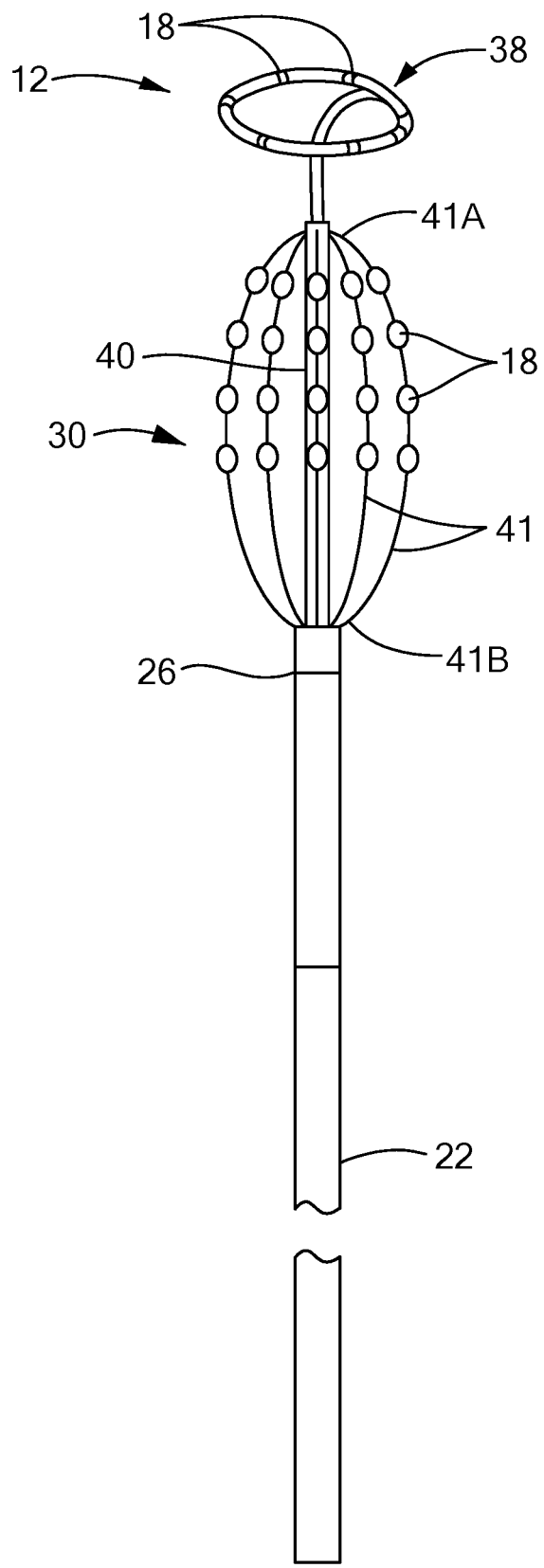
FIG. 4 shows a fourth embodiment of a medical device for electroporating tissue.

In one embodiment as shown in FIG. 4, the expandable element 30 may include one or more splines or thin flexible membranes 41. The spline(s) 41 may be used without a balloon or inflatable element, or may surrounding or be located within a balloon or inflatable element (not shown). One or more electrodes 18 may be adhered to, mounted to, affixed to, or otherwise disposed or coupled to the spline(s) 41. This may allow for smaller electrode size and enhancement of mapping signal recording. In one embodiment, the medical device 12 may include eight splines 41 (five splines of which are shown in FIG. 4), each spline 41 having a distal portion 41A and a proximal portion 41B. The distal portion 41A of each spline 41 may include a plurality of electrodes 18. The proximal portion 41B of each spline 41, and the portions of the distal portion 41A of each spline 41 located between electrodes 18, optionally may be insulated (for example, may include an insulative coating). Further, the distal portion 41A of each spline 41, such as a distal tip of each spline, may be adhered to, affixed to, or otherwise coupled to a distal portion of a lumen 40 (for example, an guidewire lumen as shown in FIG. 2), though which a secondary medical device 38 may be passed, as discussed above. Longitudinal movement of the lumen 40 within the elongate body 22 may change the size, shape, and configuration of the spline(s) 41. For example, advancement of the lumen 40 within the elongate body 22 may extend the spline(s) 41 and reduce the diameter of the expandable element 30, whereas retraction of the lumen 40 within the elongate body 22 may retract the spline(s) 41 and increase the diameter of the expandable element 30. That is, the spline(s) 41 may be transitionable between a linear, or at least substantially linear, first configuration and an expanded second configuration in which each spline 41 is curvilinear, bowed, or arcuate (for example, as shown in FIG. 4).

The energy generator 14 may be within or in electrical communication with a control unit 42 that may further include or be in electrical communication with one or more other system components, such as one or more displays 44, user input devices 46, secondary medical devices 38, a mapping and/or navigation system 48 (which may also be referred to herein as a recording system 48), the CEDS 16, and the like. For simplicity, all system components other than the medical device 12 and the secondary medical device 38 (if included in the system 10) may be collectively referred to as being part of the control unit 42. In addition to being configured to deliver ablation energy, such as electroporation energy, the plurality of electrodes 18 may also be configured to perform diagnostic functions, such as to collect intracardiac electrograms (EGM) and/or monophasic action potentials (MAPs) as well as performing selective pacing of intracardiac sites for diagnostic purposes. Recorded signals may be transferred from the device electrode energy distribution system 16 to the control unit 42. Alternatively, in some embodiments, the recorded signals may be transferred directly from the medical device 12 to the control unit 42 (for example, to the energy generator 14).

The plurality of electrodes 18 may also be configured to record impedance measurements from tissue and/or fluids surrounding and/or in contact with the electrodes 18 in order to monitor the proximity to target tissues and quality of contact with, for example, an area of target tissues CEDS 16. The plurality of electrodes 18 may also be configured to record impedance measurements from tissue before, during, and/or after the delivery of electroporation energy to determine or qualify lesion formation in the target tissue. The generally accepted definition of the term impedance is used herein: a complex ratio of sinusoidal voltage to current in an electric circuit or component, except that as used herein, impedance shall apply to any region or space through which some electrical field is applied and current flows. The generator 14 may be configured to receive impedance measurements from the plurality of electrodes 18 and use the impedance measurement to at least one of activate an electrode from the plurality of electrodes 18 or deactivate an electrode from the plurality of electrodes 18. Electrodes 18 may be activated based upon the impedance measurements during ablation. When targeted tissue is identified with the impedance measurement, energy can be delivered to those electrodes in close proximity or in contact with specified tissue and electrodes 18 which are in contact with blood or tissue that is not desirable may be deactivated based upon a specific impedance measurement. The CEDS 16 may include high speed relays to disconnect/reconnected specific electrodes 18 of the plurality of electrodes 18 from/to the generator 14 during an energy delivery procedure. In a non-limiting example, the relays may automatically disconnect/reconnect electrodes 18 to enable the medical device 12 to record mapping signals between deliveries of electroporation energy pulses.

Although not shown, the system 10 may include one or more sensors to monitor the operating parameters throughout the system, in addition to monitoring, recording or otherwise conveying measurements or conditions within the medical device 12 or the ambient environment at the distal portion of the medical device 12. For example, each electrode 18 may include a temperature sensor, pressure sensor, or other sensor. The sensor(s) may be in communication with the generator 14 and/or the CEDS 16 for, for example, initiating or triggering one or more alerts and/or therapeutic delivery modifications during operation of the medical device 12.

Electroporation is a phenomenon causing cell membranes to become "leaky" (that is, permeable for molecules for which the cell membrane may otherwise be impermeable or semipermeable). Electroporation, which may also be referred to as electropermeabilization, pulsed electric field treatment, non-thermal irreversible electroporation, irreversible electroporation, high frequency irreversible electroporation, nanosecond electroporation, or nanoelectroporation, involves the application of high-amplitude pulses to cause physiological modification (i.e., permeabilization) of the cells of the tissue to which the energy is applied. These pulses preferably may be short (for example, nanosecond, microsecond, or millisecond pulse width) in order to allow the application of high voltage, high current (for example, 20 or more amps) without long duration(s) of electrical current flow that may cause significant tissue heating and muscle stimulation. The pulsed electric energy may induce the formation of microscopic defects that result in hyper-permeabilization of the cell membrane. Depending on the characteristics of the electrical pulses, an electroporated cell can survive electroporation, referred to as "reversible electroporation," or die, referred to as "irreversible electroporation" (IEP). Reversible electroporation may be used to transfer agents, including genetic material and other large or small molecules including but not limited to therapeutic agents, into targeted cells for various purposes, including the alteration of the action potentials of cardiac myocytes.

As such, the control unit 42 may include processing circuitry 50 that includes software modules containing instructions or algorithms to provide for the automated and/or semi-automated operation and performance of various system 10 functions. For example, the processing circuitry 50 may include a processor and a memory in communication with the processor, and the memory may include instructions that, when executed by the processor, configure the processor to perform sequences, calculations, or procedures described herein and/or required for a given medical procedure. In one embodiment, the processing circuitry 50 is a component of the generator 14 within the control unit 42. The processing circuitry 50 may be further configured to deliver electroporation energy or another type of energy to the electrodes 18 and determine whether an alert condition is present. The alert condition may be based at least in part on signals received from the electrode(s) 18 (for example, impedance measurements recorded by the electrode(s) 18) and/or one or more other system sensors. In one embodiment, the generator 14 may be configured to cease the delivery of electroporation energy to one or more electrodes 18 and/or prevent the delivery of electroporation energy to one or more electrodes 18 when the processing circuitry determines the alert condition is present.

The system 10 may further include a plurality of surface electrodes 52 in communication with the generator 14 directly or indirectly through the CEDS 16. The plurality of surface electrodes 52 may be part of a positioning and navigation system that allows for the localization of the electrodes within three-dimensional space within the patient's body through the transmission and receipt of positioning and navigation signals to and from the generator 14. When the surface electrodes 52 are applied to the skin of a patient, they may be used, for example, to monitor the patient's cardiac activity to determine pulse train delivery timing at the desired portion of the cardiac cycle (that is, to record and transmit electrical activity measurements to the generator 14 and/or for navigation and location of the device 12 within the patient). The surface electrodes 52 may be in communication with the generator 14 for determining the timing during a cardiac cycle at which to initiate or trigger one or more alerts or therapeutic deliveries during operation of the medical device 12. In addition to monitoring, recording, or otherwise conveying measurements or conditions within the medical device 12 or the ambient environment at the distal portion 26 of the medical device 12 (for example, electrocardiogram or ECG signals and/or monophasic action potentials or MAPs), the surface electrodes 52 may be used to record measurements such as temperature, electrode-tissue interface impedance, delivered charge, current, power, voltage, work, or the like. An additional neutral electrode patient ground patch (not shown) may be used to evaluate the desired bipolar electrical path impedance, as well as monitor and alert the operator upon detection of undesired and/or unsafe conditions. As used herein, the term "bipolar ablation" or "bipolar energy" may refer to the delivery of electric pulses between two electrodes (for example, between two electrodes 18 of the medical device 12), rather than between a single device electrode and a ground electrode (for example, as is the case in unipolar ablation). The generator 14 may be configured to deliver a sampling pulse prior to delivery of a full series or "pulse train" of pulsed electric field ablative therapy pulses. Such a preliminary sampling pulse may provide measurements of relative electrical impedance between electrodes and warning of inappropriate electrode configurations such as overlapping electrodes and/or electrodes that are positioned too closely together and that could result in, for example, a short circuit condition. The medical device 12 may be configured to deactivate certain electrodes 18 if they are overlapping and/or positioned too closely together. Additionally, such preliminary pulses may be used to evaluate such conditions as relative proximity of individual electrodes 18 to ensure an appropriate voltage is to be applied to the electrodes during subsequent energy delivery and the voltage that is delivered to the electrodes 18 may be adjusted. These preliminary pulses may also be applied to assess whether the electrodes are positioned properly relative to the target tissue allowing the electrodes 18 to be repositioned in relation to the target tissue. The preliminary pulses may be delivered with or without automated, immediate, subsequent delivery of one or more therapeutic pulse trains.

When the medical device 12 is initially positioned before initiation of a delivery of electroporation energy, one or more checks may be performed to determine whether the expandable element 30 and/or electrodes 18 are optimally positioned to ablate an area of target tissue without causing unintended damage to non-target tissue and/or damage to the medical device 12 or generator 14. The check(s) may fail if the processing circuitry 50 determines one or more alert conditions are present. In one non-limiting example, the medical device 12 may be navigated to a target treatment site to perform an electroporation procedure, such as electroporation of cardiac tissue, renal tissue, airway tissue, and/or organs or tissue within the cardiac space. Specifically, the expandable element 30 may be expanded or collapsed (in some embodiments, inflated or deflated) and may adjust to the shape of a particular tissue region. When the expandable element 30 is expanded or inflated, the electrodes may initially deliver a sampling pulse to measure, as a non-limiting example, relative electrical impedance. Depending upon the impedance measurement, a warning may be provided (for example, an audible warning and/or a visual warning, such as a LED light or text or symbolic indication shown on one or more displays 44) to alert that certain electrodes 18 may not be properly positioned, which the processing circuitry 50 may identify as an alert condition. For example, certain electrodes 18 may be in contact with or proximate tissue that is not intended to be ablated or certain electrodes 18 may be too close to one another for the safe delivery of energy. Any electrodes 18 that have an impedance measurement that triggers the warning may be deactivated so that energy will not be delivered to those particular electrodes 18. The medical device 12 may be repositioned and another sampling pulse may measure relative electrical impedance to determine if a warning is generated for any of the electrodes 18 when the medical device is 12 in the new position. In one embodiment, impedance measurements may be recorded by each electrode 18 at each of two frequencies (for example, 12 kHz and 100 kHz) and those impedance measurements for each electrode 18 may be compared to each other, to impedance measurement(s) from other electrode(s) 18, and/or to impedance measurements recorded by supplemental electrode(s) 18', surface electrodes 52, and/or other system electrodes. If no warning is provided on the display 44, the electrodes 18 may be activated by the processing circuitry 50, thus being capable of transmitting energy from the generator 14. Additionally or alternatively, if a warning is generated for one or more electrodes 18, the processing circuitry 50 may deactivate or prevent the delivery of electroporation energy to those electrodes 18 without requiring the medical device 12 to be repositioned.

As a further non-limiting example, the system 10 may perform a check to determine whether the expandable element 30 has been properly expanded or inflated and, therefore, to determine whether there is adequate spacing between adjacent electrodes 18 for the safe and/or effective delivery of electroporation energy. When the expandable element 30 is expanded or inflated prior to the delivery of electroporation energy, portions of the expandable element 30 may not expand as intended and/or may adhere together, which may cause adjacent electrodes 18 to be located very close to each other. If electroporation energy were delivered in a bipolar fashion between electrodes without adequate spacing or that were in contact with each other, a spike in the delivered current may occur. Put another way, when there is uniform spacing between electrodes 18, the electric field between the electrodes 18 will have a uniform intensity. Additionally, delivering energy from electrodes 18 on an improperly expanded or inflated expandable element 30 (for example, an expandable element with impaired/compromised symmetry) may result in the formation of non-contiguous or non-transmural lesions. The processing circuitry 50 may identify such improper inflation as an alert condition. After the expandable element 30 is expanded (such as by inflation), a sampling pulse may be delivered to determine if the expandable element 30 has fully expanded/inflated. If there are portions of the expandable element 30 are adhering together, the impedance signal will be altered and the processing circuitry 50 may alert the user. The electrodes 18 that are associated with the altered impedance signal may be deactivated and/or the expandable element 30 may then be at least partially deflated/collapsed and then reinflated/re-expanded to full expansion. Alternatively, the medical device 12 may be removed from the patient and replaced with a new device. These checks may enable the processing circuitry 50 to determine which electrode(s) 18 should be activated or deactivated, an inflation status of the expandable element (for example, whether the expandable element has symmetrically expanded/inflated and/or whether the electrodes 18 are properly spaced from each other), whether to initiate the delivery of electroporation energy, and/or other parameters. In a similar manner, if the medical device 12 includes an expandable element 30 with splines 41, the electrodes 18 located on the splines 41 may be found to be in close proximity after expansion of the splines 41. In such a situation, the sampling pulse and impedance checks would provide a warning and/or alert the user to re-expand the splines 41 to achieve the desired uniform electrode spacing.

Once the checks have been performed and the processing circuitry 50 determines the delivery of electroporation energy should be initiated and, optionally, to which electrode(s) 18, transmission of electroporation energy from the generator 14 to the electrode(s) 18 may be commenced. The generator 14 may be configured and programmed to deliver pulsed, high-voltage electric fields appropriate for achieving reversible or irreversible electroporation. In one embodiment, the generator 14 may be configured to deliver irreversible electroporation energy that is sufficient to induce cell death for purposes of completely blocking an aberrant conductive pathway along or through cardiac tissue, destroying the ability of the cardiac tissue to propagate or conduct cardiac depolarization waveforms and associated electrical signals.

One or more electrodes 18 may record impedance measurements before, during, and/or after the delivery of electroporation energy. In one embodiment, the electrode(s) 18 that are activated and that transmit energy may be used to record impedance measurements from the area of tissue to which the energy is delivered. Additionally or alternatively, the electrode(s) 18 that are deactivated and do not transmit energy may be used to record impedance measurements from nearby tissue and/or surrounding fluid. The processing circuitry 50 may use the recorded impedance measurements to determine if the tissue to which energy has been delivered (that is, the treated tissue) has been adequately ablated. The electrode(s) 18 may continue delivering energy, or may be reactivated to deliver energy, to area(s) of tissue from which impedance measurements have been recorded that indicate sufficient ablation has not occurred.

Referring now to FIGS. 5-21, the electrodes 18 and energy delivery patterns are disclosed in more detail. In general, energy may be delivered during a medical procedure, such as an ablation procedure, in one or more of the energy delivery patterns discussed herein. These energy delivery patterns, and other energy delivery patterns not expressly disclosed herein, may be achieved by selectively deactivating one or more electrodes 18 (such as by disconnecting those electrodes 18 from both the positive and negative polarities of the generator 14) and/or activating one or more electrodes 18 (such as by connecting each of those electrodes to either the positive or negative polarity of the generator 14) disconnecting one or more electrodes 18 from the generator 14. Optionally, the electrodes 18 may be configured such that different portions of the electrode 18 may be selectively activated or deactivated. Further, the electrodes 18 may be closely spaced to each other (for example, may have spacing of between approximately 1 mm and approximately 3 mm) and may be relatively small (for example, between approximately 1.5 mm and approximately 3 mm in length), which may enhance mapping signal recording. These same electrodes 18 may also be selectively connected to/disconnected from the generator 14 to deliver electroporation energy (for example, high voltage pulses or pulse trains having a short duration).

In one general embodiment, all electrodes 18 may be connected to the mapping system 48 to record one or more mapping measurements, such as ECG signals. In this embodiment, one or more adjacent electrodes 18 may be connected to the mapping system 48 to reduce spacing between electrodes 18 activated for mapping and, therefore, to enhance signal fidelity. After the mapping measurements have been recorded, one or more electrodes 18 may be disconnected from the mapping system 48 and connected to one of the polarities of the generator 14 for the delivery of electroporation energy. When delivering electroporation energy, the electrodes 18 may be connected to the generator 14 such that electrodes immediately adjacent to each other are not both activated at the same time. This configuration may allow the generator 14 to apply relatively high voltages to electrodes 18 that are separated by adequate distance to produce a desired uniform electric field strength distribution. Alternatively, the electrodes 18 may be connected to the generator 14 such that adjacent electrodes are both activated. Alternatively, a groups of first electrodes 18 may be connected to the same polarity of the generator 14 and all other electrodes 18 (that is, a larger second group of electrodes 18) may be connected to the opposite polarity of the generator 14, which may enhance the electric field strength under the smaller first group of electrodes 18. In this way, customized energy delivery patterns may be used to create specific lesion sizes, shapes, and depths.

A number of energy delivery patterns may be used during a single medical procedure. This may cause the treated tissue to experience multiple electric field vector directions, thereby causing a larger percentage of exposed cells to become irreversibly electroporated. The processing circuitry 50 may be programmed and configured to automatically or semi-automatically switch electrode connections (for example, through the CEDS 16) multiple times during a medical procedure to deliver two or more energy delivery patterns sequentially. In one non-limiting example, the processing circuitry 50 may receive a signal by the user to initiate the procedure (which may include electroporation and/or mapping signal recording). When the procedure is initiated, the processing circuitry 50 may be configured to cause the generator 14 to deliver a train of electrical pulses where the electrical field vectoring is between closely spaced electrodes 18, and then immediately thereafter cause the generator 14 to deliver a train of electrical pulses where the electrical field vectoring is between more widely spaced electrodes 18. Each pulse train for each delivery pattern may have a duration of between approximately 10 milliseconds (ms) and approximately 100 ms. These patterns may be repeated and/or further be immediately followed by one or more other patterns, with no delay, or period in which no electroporation energy is delivered, between energy delivery patterns, or with a minimal delay (for example, approximately 10 ms) between energy delivery patterns that is not longer than the duration of the preceding pulse train. As a non-limiting example, the processing circuitry 50 may be configured to automatically deliver a sequence of two or more energy delivery patterns in rapid succession by selectively activating or deactivating each of the plurality of electrodes. In one embodiment, the processing circuitry 50 may be configured to automatically and sequentially deliver a sequence of at least five energy delivery patterns by selectively activating or deactivating each of the plurality of electrodes. In one embodiment, the processing circuitry 50 may be configured to automatically and sequentially deliver a sequence of eleven energy delivery patterns by selectively activating or deactivating each of the plurality of electrodes (for example, those energy delivery patterns shown in FIGS. 11-21). Further, the processing circuitry 50 optionally may be configured to determine whether one or more electrodes 18 are in sufficient proximity to the area of tissue and to selectively apply the energy delivery patterns to those electrodes determined to be sufficiently proximate the area of tissue.

The electrodes 18 in the plurality of electrodes 18 may be uniformly or symmetrically spaced apart from each other and radially arranged about the elongate body longitudinal axis 28 and around a circumference of the expandable element 30. Alternatively, the electrodes 18 may be un-uniformly or asymmetrically spaced apart. Uniformly spaced electrodes 18 may allow for the even distribution of electric field strength during pulsed high voltage energy deliveries and unevenly spaced electrodes 18 may allow for a variable distribution of electric field strength. Although the term "plurality" is used to refer to different groups of electrodes of the plurality of electrodes 18, it will be understood that a single electrode 18 may have the characteristics described for a particular group of electrodes. That is, for simplicity, a single electrode may be referred to as a "plurality of electrodes" for purposes of comparison to a different plurality of electrodes. Thus, a plurality of electrodes 18 as referred to herein may include at least one electrode. For example, an expandable element 30 including a plurality of electrodes 18, may include a first at least one electrode 18A and a second at least one electrode 18B. Further, the electrodes 18 may be spaced and/or distributed of splines 41 of the expandable element 30 as discussed herein, in those embodiments in which the expandable element 30 includes splines 41. That is, even though the figures show an expandable element 30 that is inflatable, it will be understood that the expandable element 30 may include one or more splines 41 in addition to or instead of the inflatable expandable element.

Referring now to FIGS. 5-10, the medical device 12 may have a first electrode configuration of electrodes that includes a plurality of teardrop-shaped electrodes 18 on the expandable element 30. Optionally, the medical device 12 may also include a distal electrode 18" at the distalmost location on the expandable element 30. Each teardrop-shaped electrode 18 may be tapered in a proximal-to-distal direction, with a first or distal end 54 that is pointed and a second or proximal end 56 that is rounded. This teardrop electrode shape may preserve consistent and uniform spacing between electrodes 18 when the expandable element 30 is inflated. In one embodiment, the plurality of teardrop-shaped electrodes 18 may be disposed over the distal portion 34 of the expandable element 30, with the wider proximal ends 56 of the electrodes 18 being at or proximate the equator 58 (for example, the widest circumference lying in a plane that is orthogonal to, or at least substantially orthogonal to, the elongate body longitudinal axis 28) of the inflated expandable element 30. Additionally, the electrodes 18 may be radially arranged about the elongate body longitudinal axis 28. In this configuration, at least a portion of each electrodes 18 may be configured to be in contact with, for example, a circumference of tissue surrounding a pulmonary vein when the expandable element 30 is positioned in contact with a pulmonary vein ostium, and at least a portion of at least some of the plurality of electrodes 18 may be configured to be in contact with a tissue wall (such as a wall of a chamber of a heart) when a lateral surface of the expandable element 30 is positioned to be in contact with the tissue wall. However, it will be understood that the electrodes 18 shown in FIGS. 5-10 may be of any suitable size, shape, and/or configuration and may be used to deliver energy delivery patterns other than those explicitly shown. Further, although sixteen electrodes 18 are shown in FIGS. 5-10, it will be understood that more or fewer electrodes may be used.

Figure 6:
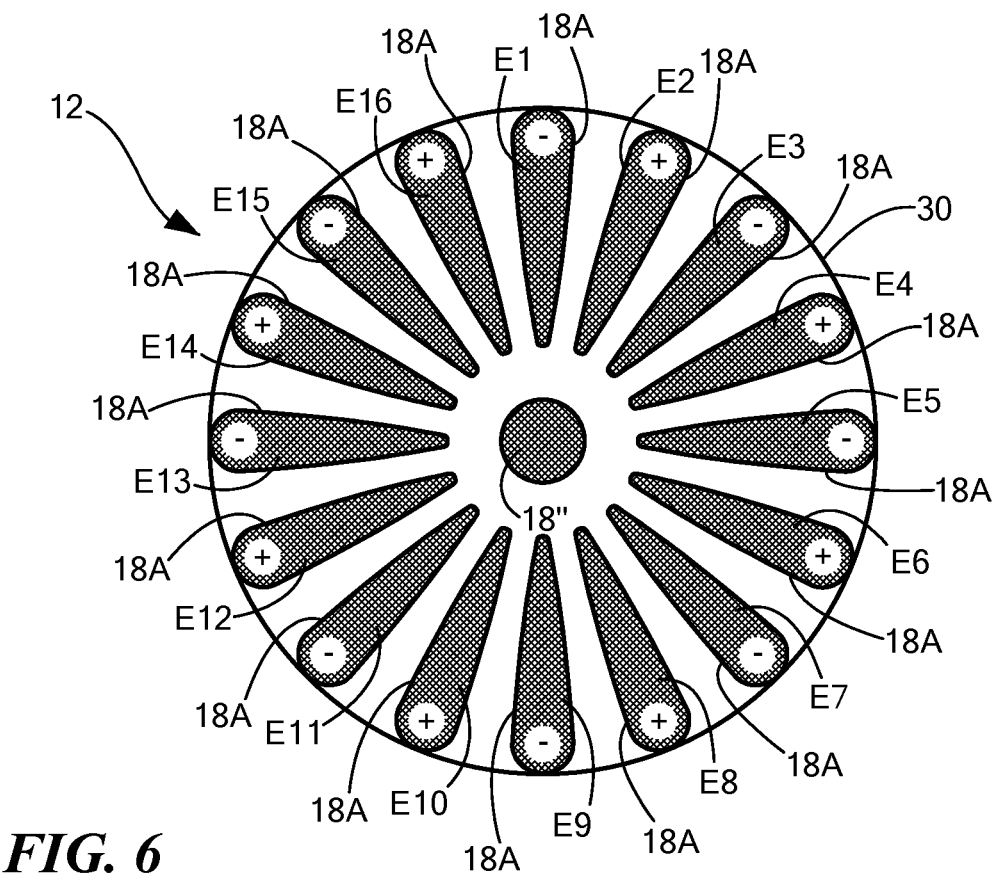
FIG. 6 shows a front view of the distal portion of the medical device shown in FIG. 3, the electrodes being activated in the first energy delivery pattern.

In a first exemplary energy delivery pattern as shown in FIGS. 5 and 6, all of the plurality of electrodes 18 may be active or coupled to one of the polarities of the generator 14. Active electrodes are referred to with reference number 18A, and these electrodes 18A are also shaded in the figures, and inactive electrodes (electrodes that are uncoupled from both polarities of the generator 14) are referred to with reference number 18B in FIGS. 5-21. Inactivating certain electrodes 18B in these energy delivery patterns may not only allow electroporation energy to be delivered in a desired pattern, but may also affect the current density at one or more locations, prevent loss of current into the blood and/or the formation of coagulum, prevent overheating of certain electrodes, and/or affect the depth of electrical field penetration into tissue. Further, every other electrode 18A may be connected to a first (for example, positive) polarity of the generator 14, and the intervening electrodes 18A may be connected to a second (for example, negative) polarity of the generator 14. The electrodes 18 are each further identified with the numbers E1-E16, representing the sixteen electrodes shown in FIGS. 5-10. The symbol "+" is used to depict electrodes in communication with the positive polarity and the symbol "−" is used to depict electrodes in communication with the negative polarity. However, it will be understood that opposite polarities of those shown in FIGS. 5-21 may be used for each electrode. In the energy delivery pattern shown in FIGS. 5 and 6, all electrodes 18A may be active, with electrodes E1, E3, E5, E7, E9, E11, E13, and E15 being connected to the negative polarity of the generator 14 and electrodes E2, E4, E6, E8, E10, E12, E14, and E16 being connected to the positive polarity of the generator 14. In this configuration, bipolar energy may be delivered between adjacent pairs of active electrodes 18A with opposite polarities, such as between electrodes E1 and E2, between electrodes E2 and E3, between electrodes E3 and E4, and so on. As adjacent electrodes 18A may be active, this configuration may be useful for recording mapping signals because of the reduced spacing between active electrode pairs. Additionally or alternatively, the electrodes 18A may be used to deliver electroporation energy.

Figure 7:
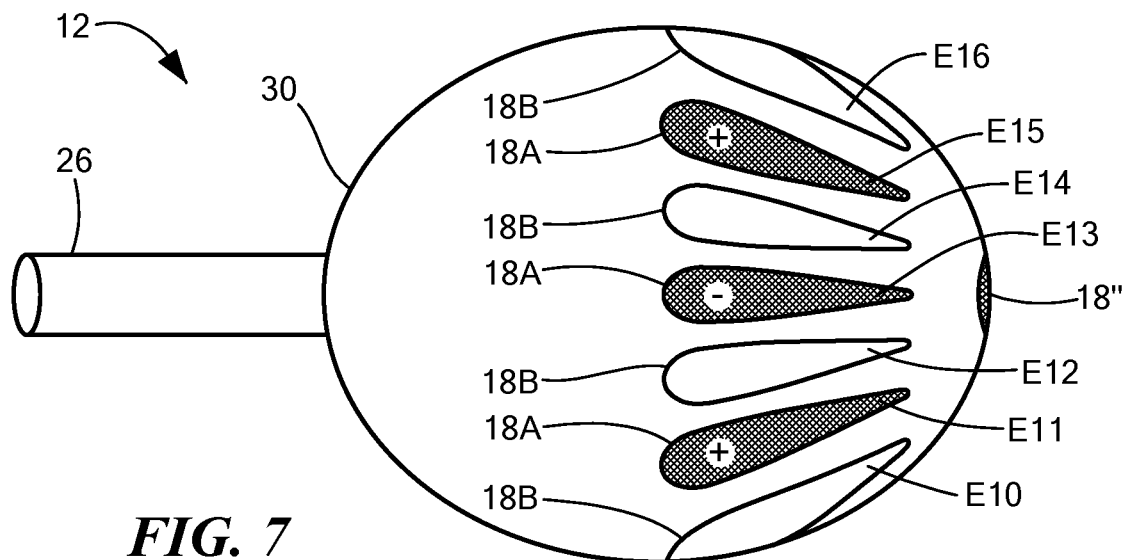
FIG. 7 shows a side view of a distal portion of a medical device having the first configuration of electrodes, the electrodes being activated in a second energy delivery pattern.
Figure 8:
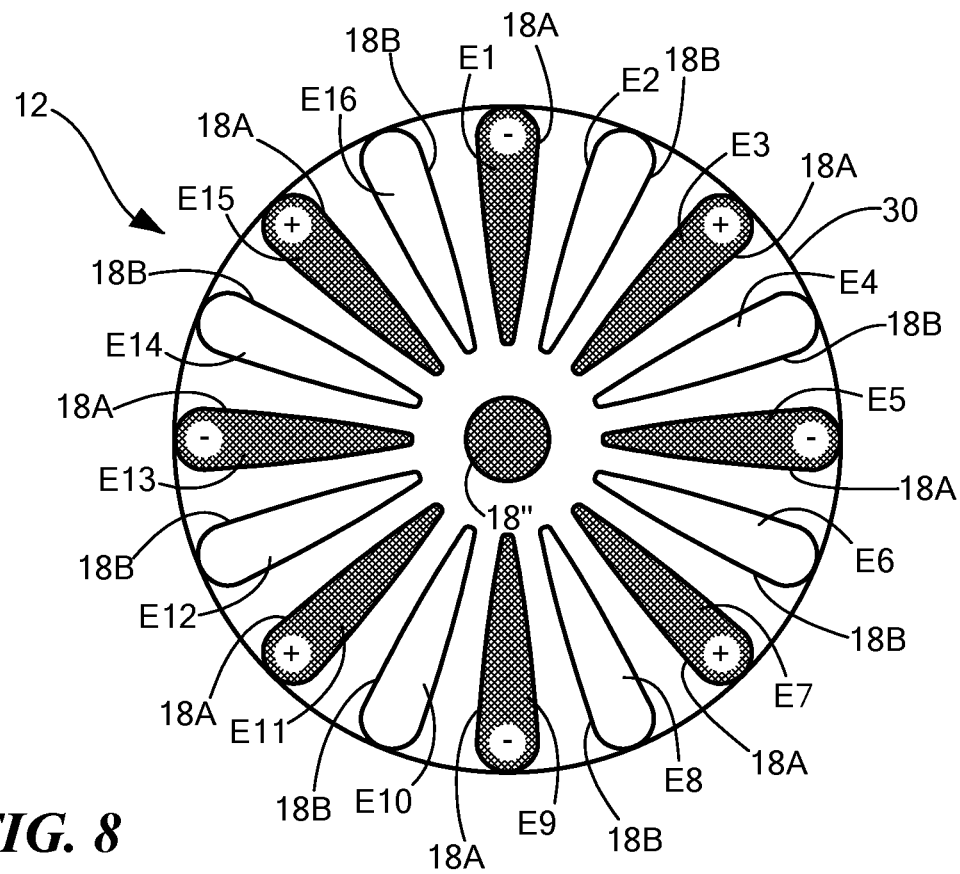
FIG. 8 shows a front view of the distal portion of the medical device shown in FIG. 5, the electrodes being activated in the second energy delivery pattern.

In a second exemplary energy delivery pattern as shown in FIGS. 7 and 8, fewer than all of the electrodes 18 may be active (that is, a first plurality of electrodes 18A may be active), with the remaining electrodes (that is, a second plurality of electrodes 18B) being inactive or uncoupled from the generator 14. Inactive electrodes are referred to with reference number 18B in FIGS. 5-21. In the energy delivery pattern shown in FIGS. 7 and 8, every other electrode 18A may be active and connected to the generator 14 (electrodes E1, E3, E5, E7, E9, E11, E13, and E15). Of these, every other active electrode 18A may be connected to the negative polarity of the generator 14 (electrodes E1, E5, E9, and E13) and the intervening active electrodes may be connected to the positive polarity of the generator 14 (electrodes E3, E7, E11, and E15). The inactive electrodes 18B may be electrodes E2, E4, E6, E8, E10, E12, E14, and E16. In this configuration, bipolar energy may be delivered between adjacent pairs of active electrodes 18A with opposite polarities, such as between electrodes E1 and E3, between electrodes E3 and E5, between electrodes E5 and E7, and so on. The increased distance between active electrode pairs may help drive the electroporation energy deeper into the target tissue than the energy delivery pattern shown in FIGS. 5 and 6.

Figure 9:
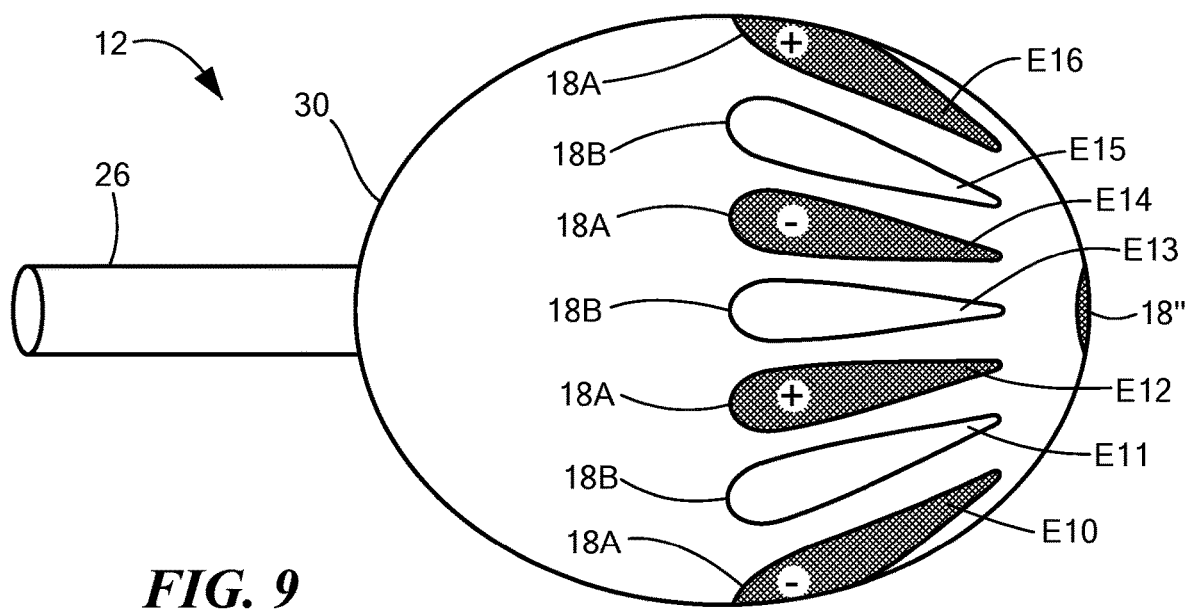
FIG. 9 shows a side view of a distal portion of a medical device having the first configuration of electrodes, the electrodes being activated in a third energy delivery pattern.
Figure 10:
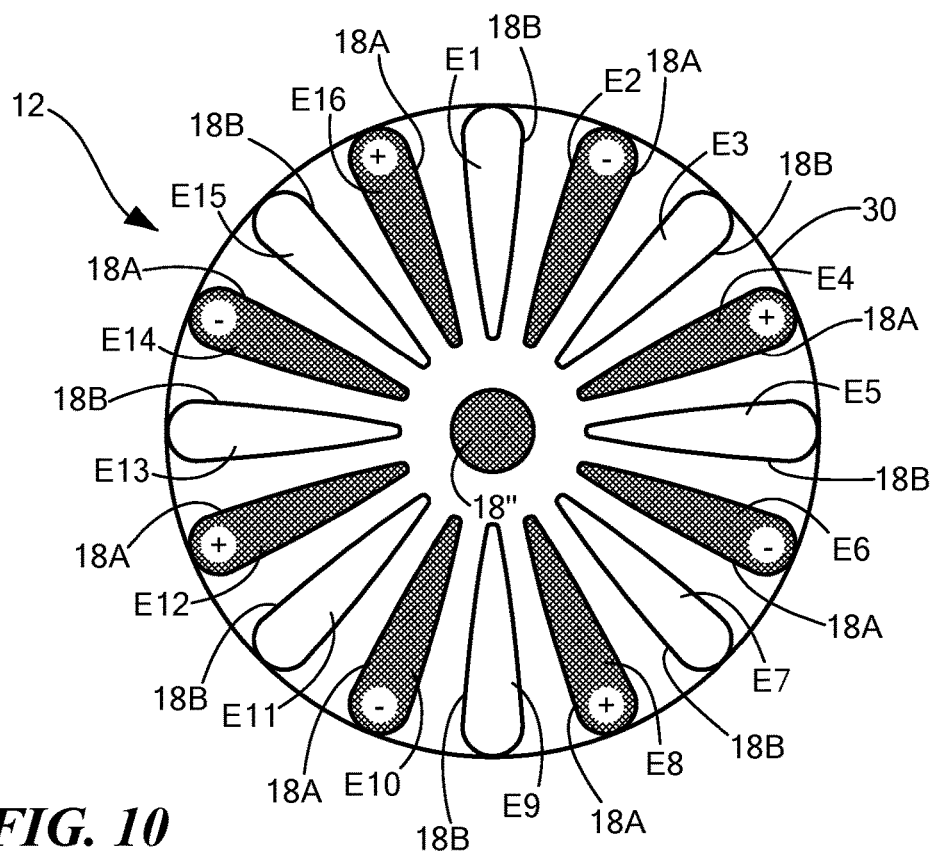
FIG. 10 shows a front view of the distal portion of the medical device shown in FIG. 7, the electrodes being activated in the third energy delivery pattern.

In a third exemplary energy delivery pattern as shown in FIGS. 9 and 10, fewer than all of the electrodes 18 may be active, with the remaining electrodes being inactive or uncoupled from the generator 14. The groups of active 18A and inactive 18B electrodes may be the opposite of those groups shown in FIGS. 7 and 8. In the energy delivery pattern shown in FIGS. 9 and 10, every other electrode 18A may be active and connected to the generator 14 (electrodes E2, E4, E6, E8, E10, E12, E14, and E16). Of these, every other active electrode 18A may be connected to the negative polarity of the generator 14 (electrodes E2, D6, E10, and E14) and the intervening active electrodes may be connected to the positive polarity of the generator 14 (electrodes E4, E8, E12, and D16). The inactive electrodes 18B may be electrodes E1, E3, E5, E7, E9, E11, E13, and E15. In this configuration, bipolar energy may be delivered between adjacent pairs of active electrodes 18A with opposite polarities, such as between electrodes E2 and E4, between electrodes E4 and E6, between electrodes E6 and E8, and so on.

Referring now to FIGS. 11-21, the medical device 12 may have a second electrode configuration of electrodes that includes a plurality of round electrodes 18 on the expandable element 30. As a non-limiting example, the plurality of electrodes 18 may be disposed over the distal portion 34 of the expandable element and may be radially arranged about the elongate body longitudinal axis 28. Although the electrodes may be disposed around an entirety of a circumference of the expandable element 30, twenty-four electrodes are shown in the side views of FIGS. 11-21 and will be specifically discussed herein for simplicity. Additionally, the electrodes shown in FIGS. 11-21 will be referred to as being in one of four series S1-S4, with each series extending around an entirety of a circumference of the expandable element 30. It will be understood that more or fewer electrodes than those shown may be used, and that other electrode sizes, shapes, and/or configurations may be used. As in FIGS. 5-10, the active electrodes 18A are shaded in FIGS. 11-21. Inactive electrodes 18B are not shaded.

Figure 11:
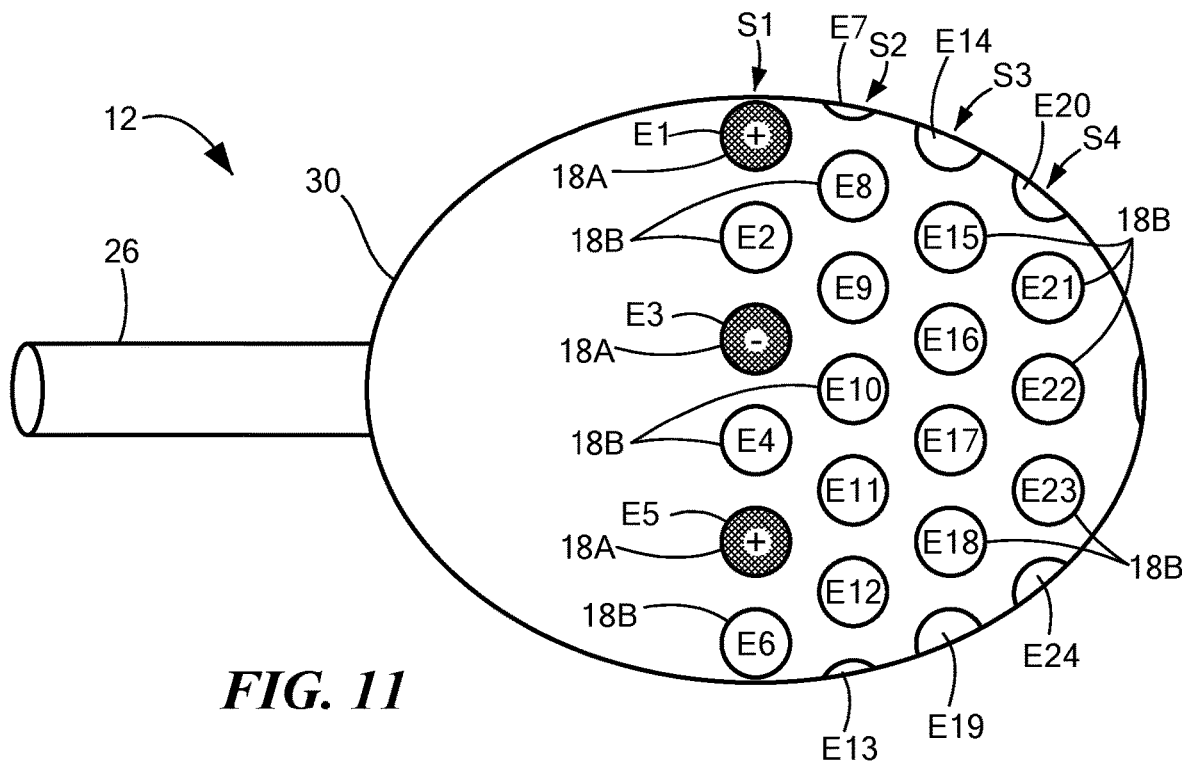
FIG. 11 shows a side view of a distal portion of a medical device having a second configuration of electrodes, the electrodes being activated in a first energy delivery pattern.

In a first exemplary energy delivery pattern as shown in FIG. 11, fewer than all of the electrodes 18 may be active, with the remaining electrodes being inactive or uncoupled from the generator 14. The active electrodes 18A may be at least some of those electrodes in series S1. For example, every other electrode 18A may be active and connected to the generator 14 (electrodes E1, E3, E5, for example). Of these, every other active electrode 18A may be connected to the negative polarity of the generator 14 (electrode E3, for example) and the intervening active electrodes 18A may be connected to the positive polarity of the generator 14 (electrodes E1 and E5, for example). The inactive electrodes 18B may be, for example, electrodes E2, E4, and E6 of series S1 and all electrodes of all of series S2-S4 (E7-E24, for example). In this configuration, bipolar energy may be delivered between adjacent pairs of active electrodes 18A in series S1 with opposite polarities that are located around the circumference of the expandable element 30.

Figure 12:
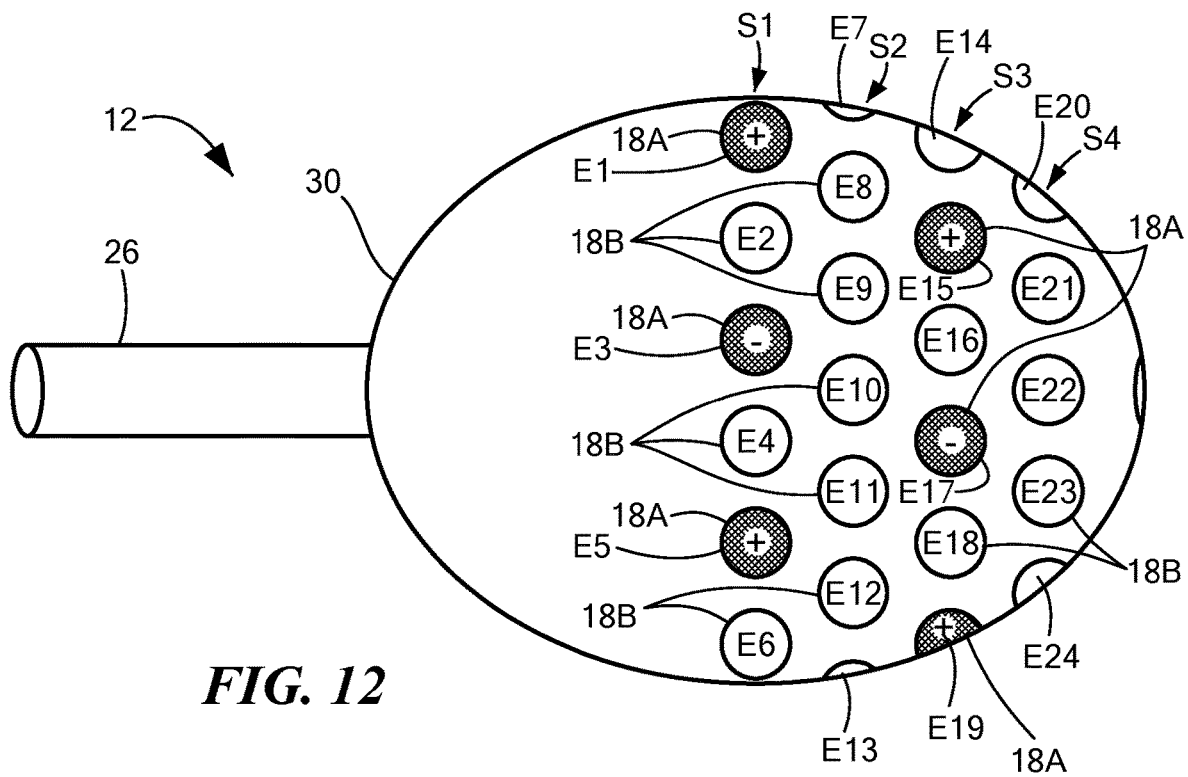
FIG. 12 shows a side view of a distal portion of a medical device having the second configuration of electrodes, the electrodes being activated in a second energy delivery pattern.

In a second exemplary energy delivery pattern as shown in FIG. 12, fewer than all of the electrodes 18 may be active, with the remaining electrodes being inactive or uncoupled from the generator 14. The active electrodes 18A may be at least some of those electrodes in series S1 and S3. For example, every other electrode 18A may be active and connected to the generator 14 (electrodes E1, E3, E5, E15, E17, and E19, for example). Of these, every other active electrode 18A may be connected to the negative polarity of the generator 14 (electrodes E3 and E17, for example) and the intervening active electrodes 18A may be connected to the positive polarity of the generator 14 (electrodes E1, E5, E15, and E19, for example). The inactive electrodes 18B may be, for example, electrodes E2, E4, and E6 of series S1, electrodes E14, E16, and E18 of series S3, and all electrodes of all of series S2 and S4 (E7-E13 and E20-E24, for example). In this configuration, bipolar energy may be delivered between adjacent pairs of active electrodes 18A in series S1 with opposite polarities, between adjacent pairs of active electrodes 18A in series S3 with opposite polarities, and between electrodes with opposite polarities between series S1 and S3.

Figure 13:
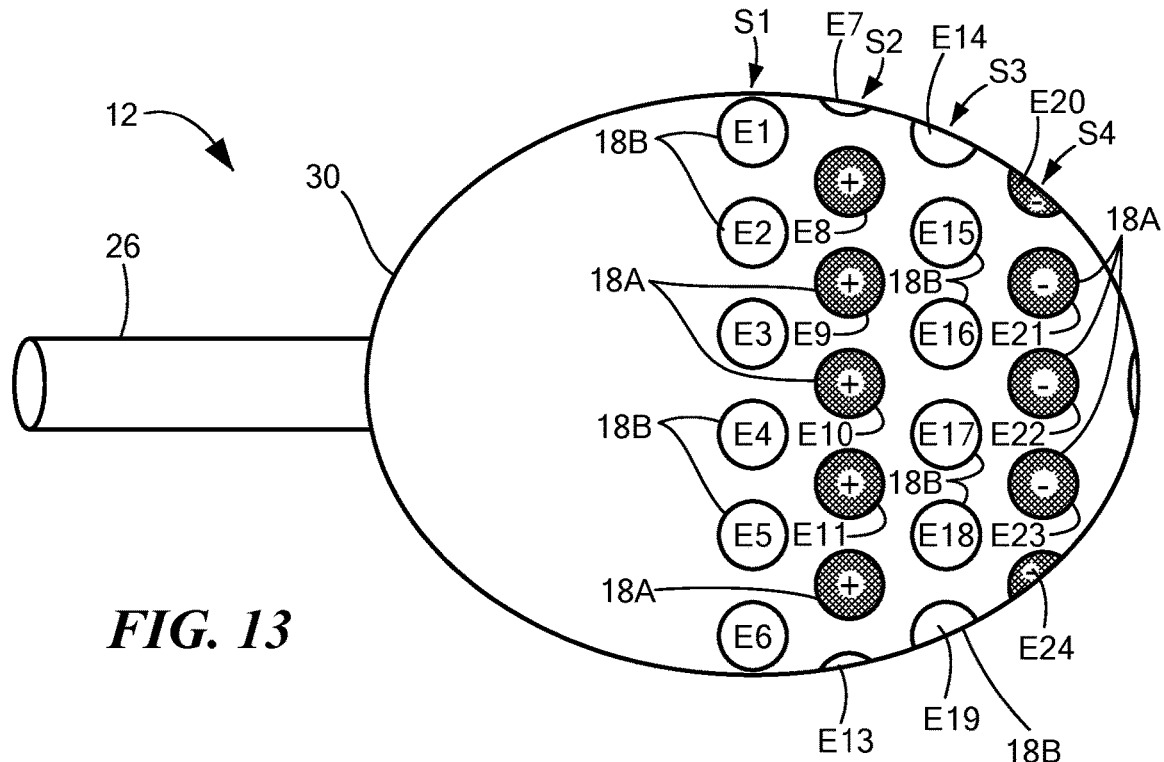
FIG. 13 shows a side view of a distal portion of a medical device having the second configuration of electrodes, the electrodes being activated in a third energy delivery pattern.

In a third exemplary energy delivery pattern as shown in FIG. 13, fewer that all of the electrodes 18 may be active, with the remaining electrodes being inactive or uncoupled from the generator 14. The active electrodes 18A may be all electrodes in series S2 (electrodes E7-E13, for example) and all electrodes in series S4 (electrodes E20-E24, for example). All electrodes 18A in series S2 may be connected to the positive polarity of the generator 14 and all electrodes 18A in series S4 may be connected to the negative polarity of the generator 14. All electrodes 18B in series S1 and S3 may be inactive.

Figure 14:
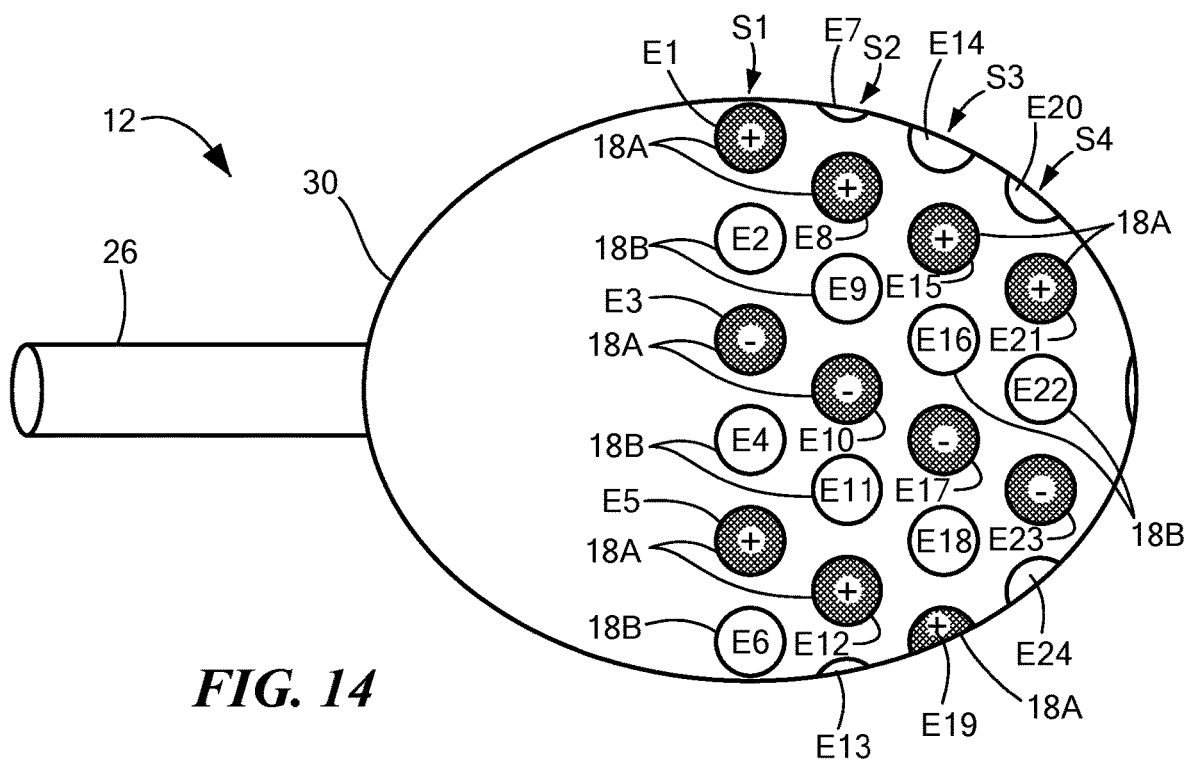
FIG. 14 shows a side view of a distal portion of a medical device having the second configuration of electrodes, the electrodes being activated in a fourth energy delivery pattern.

In a fourth exemplary energy delivery pattern as shown in FIG. 14, fewer than all of the electrodes 18 may be active, with the remaining electrodes being inactive or uncoupled from the generator 14. The active electrodes 18A may be every other electrode in series S1 (electrodes E1, E3, and E5, for example), every other electrode in series S2 (electrodes E8, E10, and E12, for example), every other electrode in series S3 (electrodes E15, E17, and E19, for example), and every other electrode in series S4 (electrodes E21 and E23, for example). Of these active electrodes 18A, every other electrode 18A may be connected to the negative polarity of the generator 14 and the intervening active electrodes 18A may be connected to the positive polarity of the generator 14. The remaining electrodes in series S1-S4 may be inactive.

Figure 15:
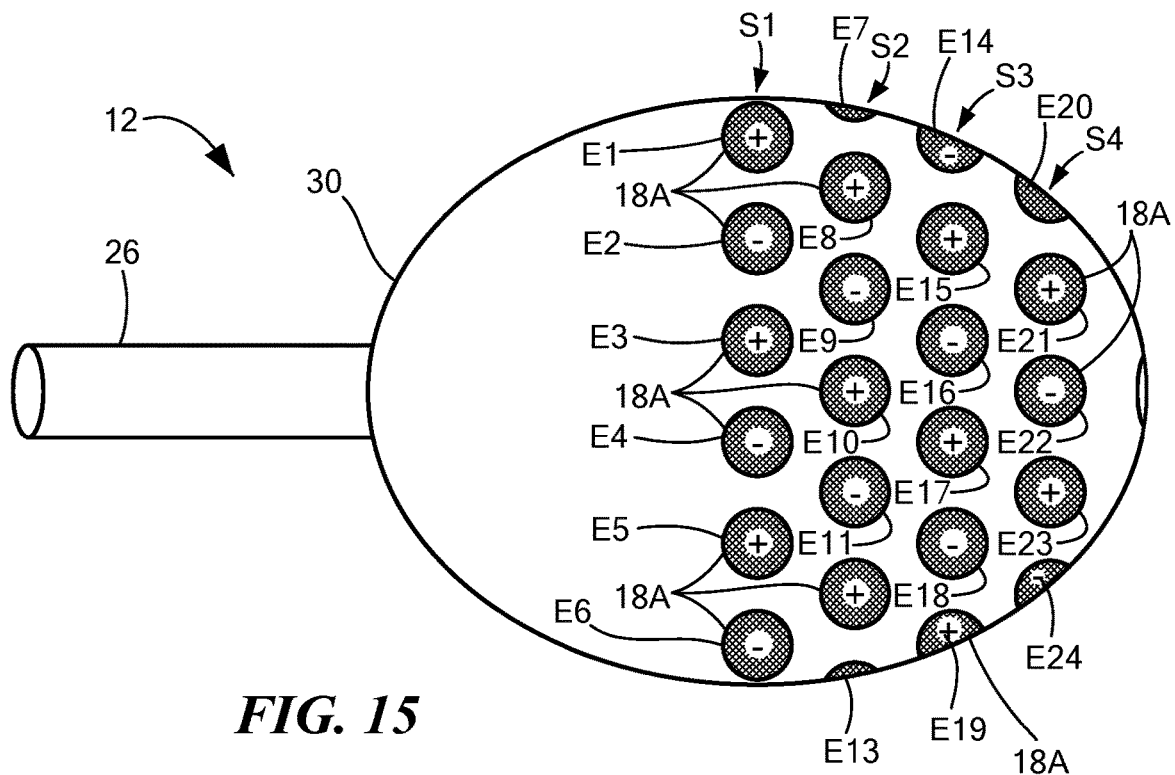
FIG. 15 shows a side view of a distal portion of a medical device having the second configuration of electrodes, the electrodes being activated in a fifth energy delivery pattern.

In a fifth exemplary energy delivery pattern as shown in FIG. 15, all of the electrodes 18 may be active. Every other active electrode 18A of each of series S1-S4 may be connected to the negative polarity of the generator 14 and the intervening active electrodes 18A may be connected to the positive polarity of the generator 14 (electrodes E1, E5, E15, and E19, for example). The inactive electrodes 18B may be, for example, electrodes E2, E4, and E6 of series S1, electrodes E14, E16, and E18 of series S3, and all electrodes of all of series S2 and S4 (E7-E13 and E20-E24, for example). In this configuration, bipolar energy may be delivered between adjacent pairs of active electrodes 18A in series S1 with opposite polarities, between adjacent pairs of active electrodes 18A in series S3 with opposite polarities, and between electrodes with opposite polarities between series S1 and S3.

Figure 16:
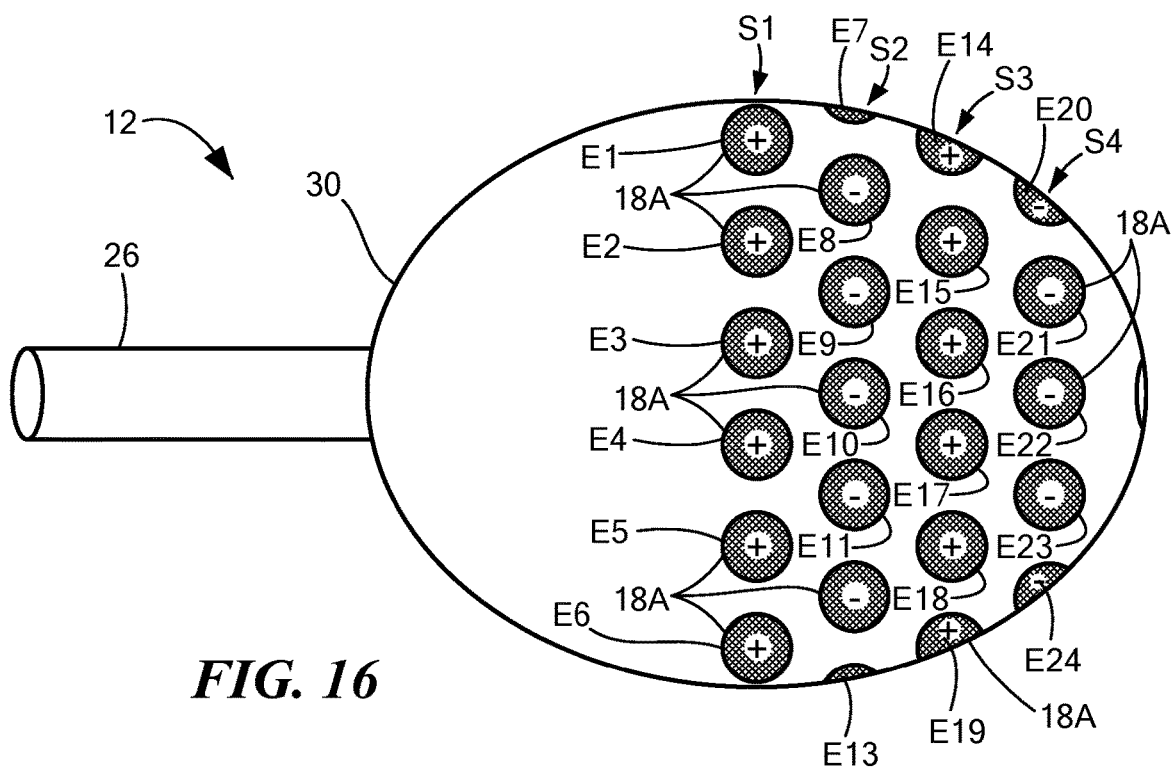
FIG. 16 shows a side view of a distal portion of a medical device having the second configuration of electrodes, the electrodes being activated in a sixth energy delivery pattern.

In a sixth exemplary energy delivery pattern as shown in FIG. 16, all of the electrodes 18 may be active. Every electrode 18A of each of series S2 and S4 may be connected to the negative polarity of the generator 14 and every electrode 18A of each of series S1 and S3 may be connected to the positive polarity of the generator 14 (electrodes E1, E5, E15, and E19, for example).

Figure 17:
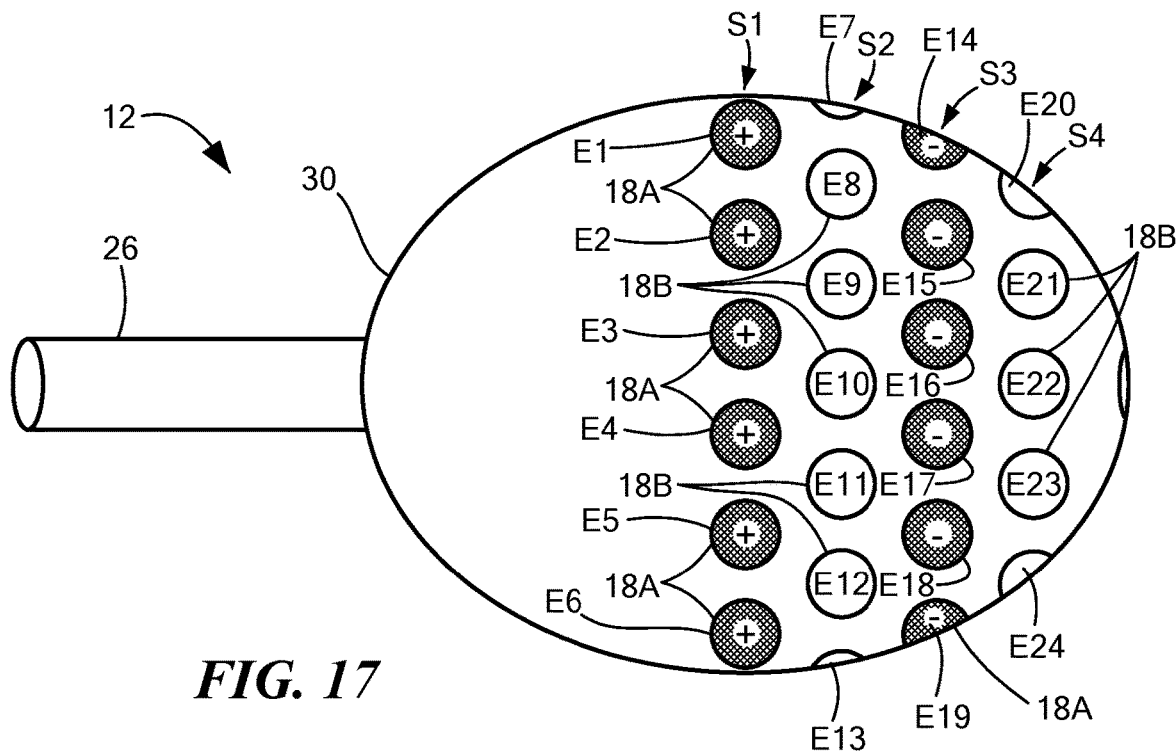
FIG. 17 shows a side view of a distal portion of a medical device having the second configuration of electrodes, the electrodes being activated in a seventh energy delivery pattern.

In a seventh exemplary energy delivery pattern as shown in FIG. 17, fewer than all of the electrodes 18 may be active, with the remaining electrodes being inactive or uncoupled from the generator 14. The active electrodes 18A may all electrodes in series S1 and S3, with the electrodes 18A in series S1 being connected to the positive polarity of the generator 14 and the electrodes 18A in series S3 being connected to the negative polarity of the generator 14. The remaining electrodes in series S2 and S4 may be inactive.

Figure 18:
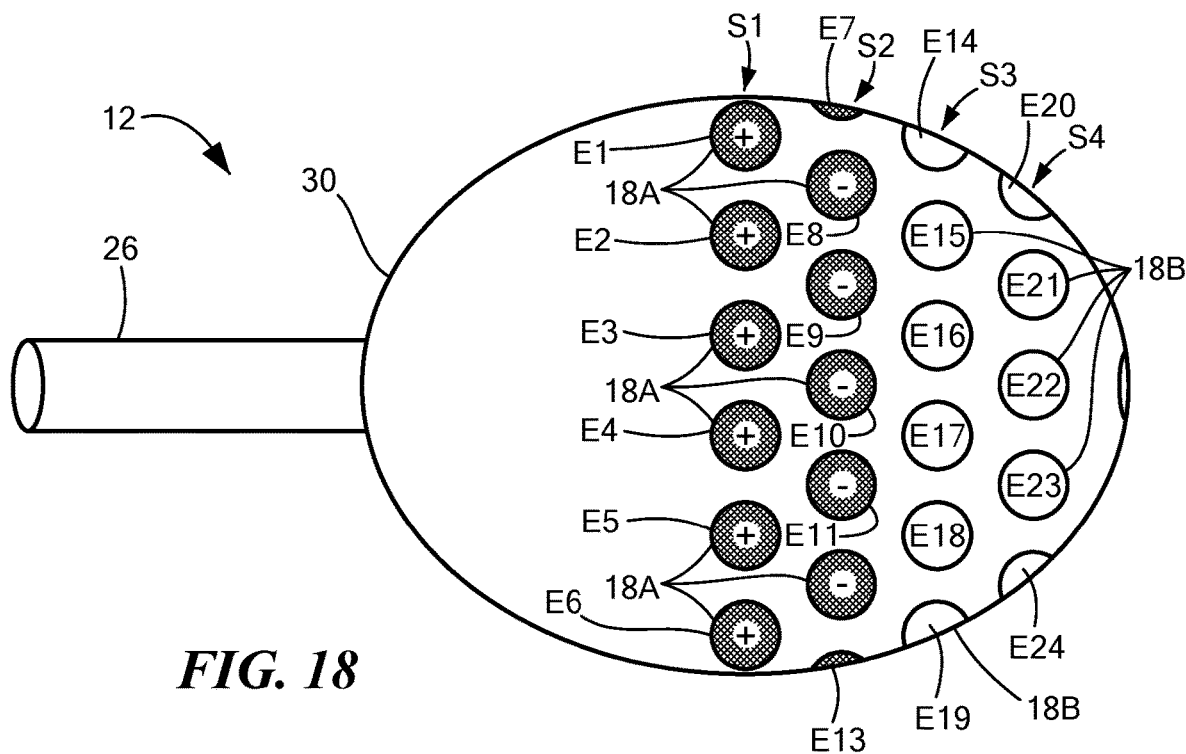
FIG. 18 shows a side view of a distal portion of a medical device having the second configuration of electrodes, the electrodes being activated in an eighth energy delivery pattern.

In an eighth exemplary energy delivery pattern as shown in FIG. 18, fewer than all of the electrodes 18 may be active, with the remaining electrodes being inactive or uncoupled from the generator 14. The active electrodes 18A may all electrodes in series S1 and S2, with the electrodes 18A in series S1 being connected to the positive polarity of the generator 14 and the electrodes 18A in series S2 being connected to the negative polarity of the generator 14. The remaining electrodes in series S3 and S4 may be inactive.

Figure 19:
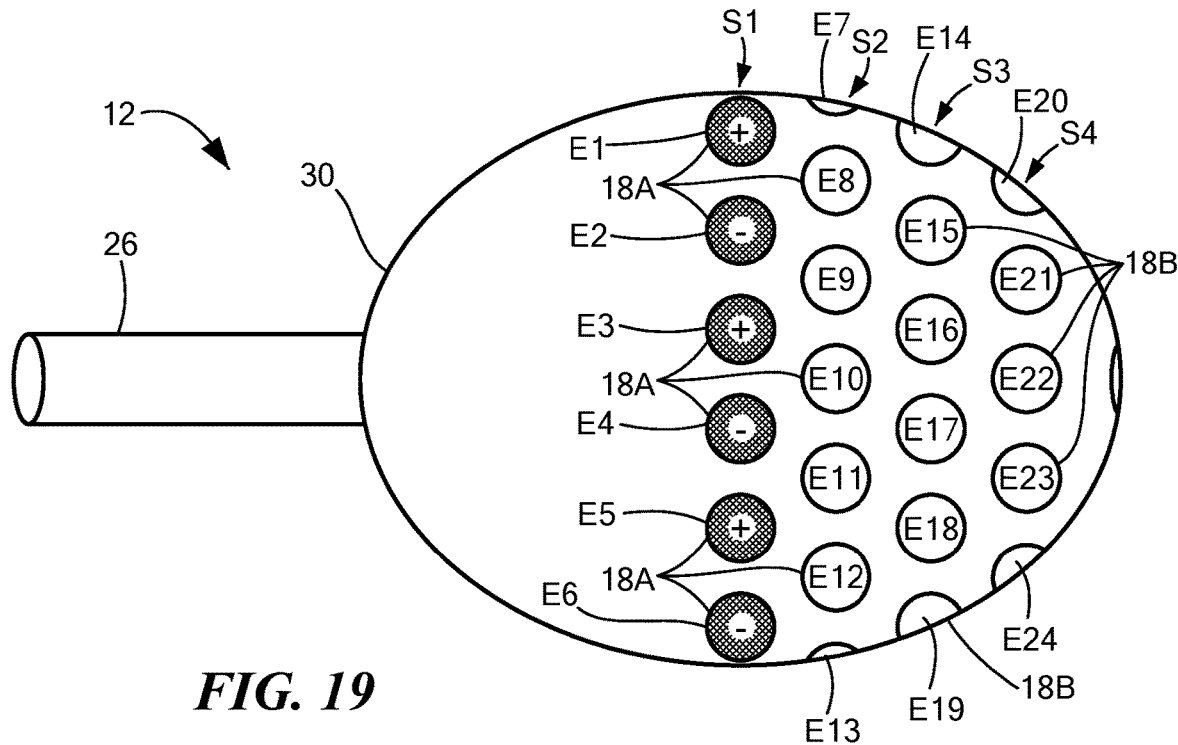
FIG. 19 shows a side view of a distal portion of a medical device having the second configuration of electrodes, the electrodes being activated in a ninth energy delivery pattern.

In a ninth exemplary energy delivery pattern as shown in FIG. 19, fewer than all of the electrodes 18 may be active, with the remaining electrodes being inactive or uncoupled from the generator 14. The active electrodes 18A may be all electrodes in series S1. Of these, every other active electrode 18A may be connected to the negative polarity of the generator 14 and the intervening active electrodes 18A may be connected to the positive polarity of the generator 14. The inactive electrodes 18B may be all electrodes of series S2-S4.

Figure 20:
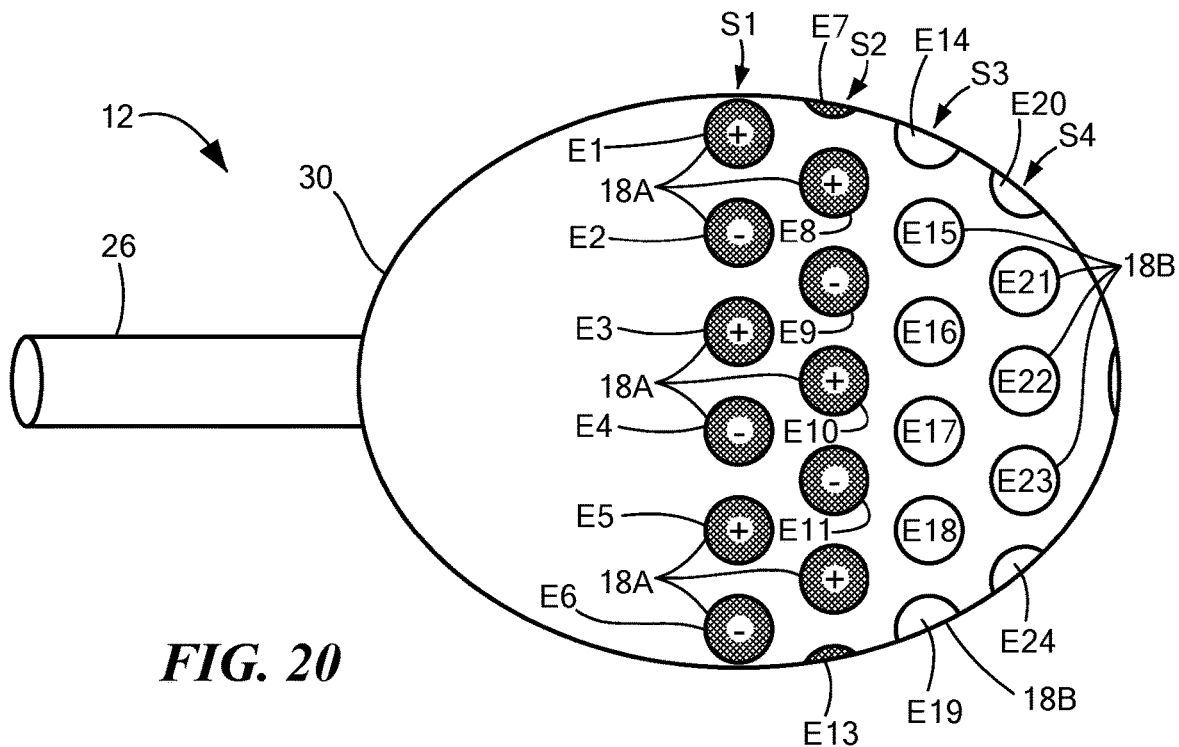
FIG. 20 shows a side view of a distal portion of a medical device having the second configuration of electrodes, the electrodes being activated in a tenth energy delivery pattern.

In a tenth exemplary energy delivery pattern as shown in FIG. 20, fewer than all of the electrodes 18 may be active, with the remaining electrodes being inactive or uncoupled from the generator 14. The active electrodes 18A may be all electrodes in series S1 and S2. Of these, every other active electrode 18A may be connected to the negative polarity of the generator 14 and the intervening active electrodes 18A may be connected to the positive polarity of the generator 14. The inactive electrodes 18B may be all electrodes of series S3 and S4.

Figure 21:
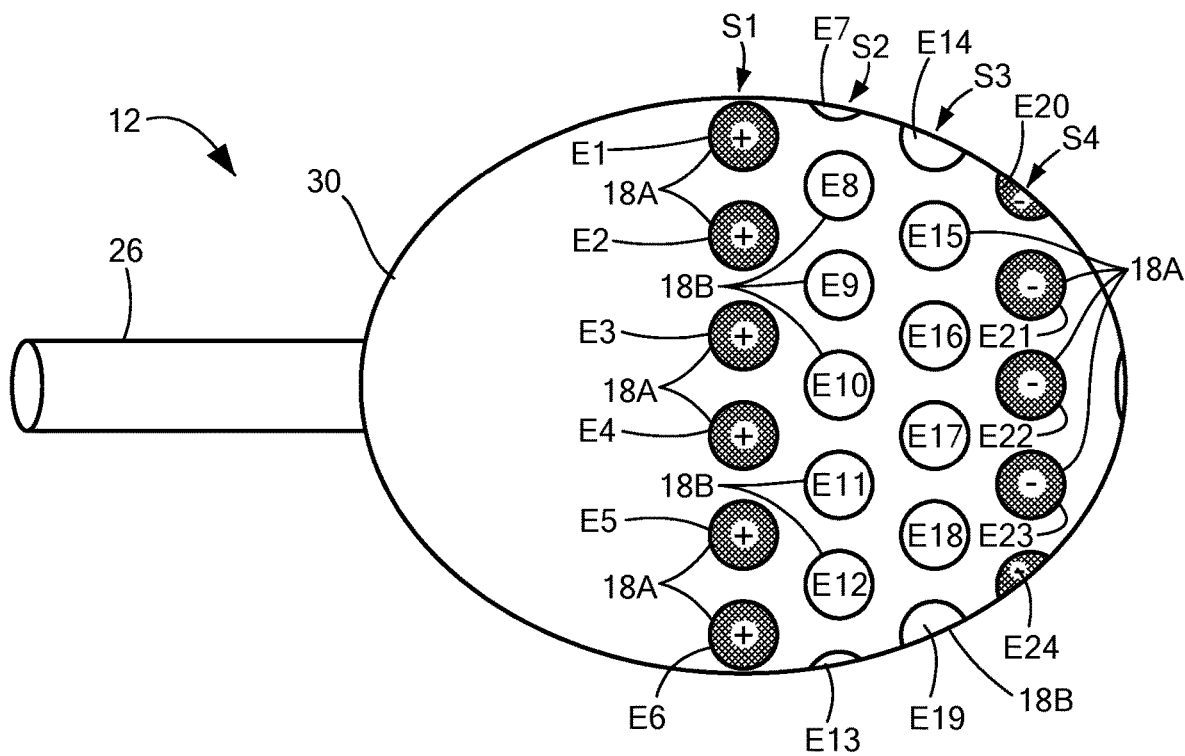
FIG. 21 shows a side view of a distal portion of a medical device having the second configuration of electrodes, the electrodes being activated in an eleventh energy delivery pattern.

In an eleventh exemplary energy delivery pattern as shown in FIG. 21, fewer than all of the electrodes 18 may be active, with the remaining electrodes being inactive or uncoupled from the generator 14. The active electrodes 18A may be all electrodes in series S1 and S4. All electrodes 18A in series S1 may be connected to the positive polarity of the generator 14 and all electrodes 18A in series S4 may be connected to the negative polarity of the generator 14. The inactive electrodes 18B may be all electrodes of series S2 and S3.

As a non-limiting example, after a train of biphasic pulses has been delivered in a first delivery pattern (for example, as shown in FIG. 11), the processing circuitry 50 and/or CEDS 16 may then switch electrode connection(s) to the generator 14 such that energy is delivered in a second energy delivery pattern (for example, as shown in FIG. 12). After a train of biphasic pulses has been delivered in the second delivery pattern, the processing circuitry 50 and/or CEDS 16 may then switch electrode connection(s) to the generator 14 such that energy is delivered in a third delivery pattern (for example, as shown in FIG. 13), and so on. The use of multiple delivery patterns at the same positioning of the expandable element 30 on the tissue surface may cause the underlying tissue to experience multiple electric field vector directions, thereby causing a larger percentage of cells exposed to electroporation and effectively electroporated. The delivery of energy in a sequence of multiple energy delivery patterns may be automated controlled by the processing circuitry 50 and may be accomplished by switching which electrodes 18 are connected to each polarity from the generator 14 with high-voltage vacuum relays or the like.

The medical device 10 may energize specific electrodes 18 with selected polarities or may combine groups of electrodes for pulsed electric field delivery. Using the various energy delivery patterns as shown in FIGS. 5-21, a fully circumferential lesion may be created when the electrodes 18 are activated or a localized lesion that is not circumferential can be created. Contiguous transmural lesions, which may be located deep within or at the surface of target tissue, may be created with these, or other, energy delivery patterns. These are non-limiting examples of different energy delivery patterns that may be used so that very specific areas of tissue can be ablated. As a non-limiting example, the energy delivery patterns may be delivered to tissue in quick succession. Alternatively, a single energy delivery pattern or series of energy delivery patterns may be repeatedly delivered to target tissue.

In one embodiment, a medical system 10 includes a medical device 12 configured to electroporate tissue, the medical device 12 including an expandable element 30, the expandable element 30 having a plurality of electrodes 18; and an energy generator 14 in communication with the plurality of electrodes 18, the energy generator 14 having processing circuitry 50 configured to: deliver electroporation energy to the plurality of electrodes 18; receive data from the plurality of electrodes 18; determine whether an alert condition is present based on the data received from the plurality of electrodes 18; and at least one of cease a delivery of electroporation energy to the plurality of electrodes 18 and prevent the delivery of electroporation energy to the plurality of electrodes 18 when the processing circuitry 50 determines the alert condition is present.

In one aspect of the embodiment, the data includes impedance measurements.

In one aspect of the embodiment, the plurality of electrodes is configured to be uniformly spaced when the expandable element 30 is expanded.

In one aspect of the embodiment, each of the plurality of electrodes 18 is configured to record at least one impedance measurement, the processing circuitry 50 being configured to receive the at least one impedance measurement from each of the plurality of electrodes 18 and selectively activate at least one of the plurality of electrodes 18 based on the at least one impedance measurement received from each of the plurality of electrodes 18.

In one aspect of the embodiment, the system 10 further includes a mapping system 48, and the energy generator and processing circuitry are further configured to selectively connect each of the plurality of electrodes to the mapping system 48 and record intracardiac electrogram signals from each of the plurality of electrodes 18.

In one aspect of the embodiment, the expandable element 30 has a distal portion 34 and a proximal portion 32, the plurality of electrodes 18 being disposed on the distal portion 34 of the expandable element 30.

In one aspect of the embodiment, the medical device 12 may further include at least one electrode 18 distal to the expandable element 30.

In one aspect of the embodiment, the at least one electrode 18 distal to the expandable element 30 is on a secondary medical device 38 that is positionable distal to the medical device 12.

In one aspect of the embodiment, the medical device 12 further includes a distal tip 39 that extends distally beyond the expandable element 30, the at least one electrode 18 distal to the expandable element 30 being on the distal tip 39.

In one aspect of the embodiment, the energy generator 14 is configured to deliver electroporation energy to the plurality of electrodes 18 in a sequence of a plurality of energy delivery patterns.

In one aspect of the embodiment, the processing circuitry 50 is configured to automatically switch between the plurality of energy delivery patterns such that a pulse train of electroporation energy is delivered in each of the plurality of energy delivery patterns at least once when the system 10 is in use.

In one aspect of the embodiment, the medical device 12 further includes a longitudinal axis 28, each of the plurality of electrodes 18 having a teardrop shape that is tapered in a proximal-to-distal direction, the plurality of electrodes 18 being radially arranged around the longitudinal axis 28.

In one embodiment, a medical system 10 includes a medical device 12 configured to electroporate an area of tissue, the medical device 12 including: a balloon 30 having a distal portion 34 and a proximal portion 32; and a plurality of electrodes 18 disposed on the distal portion 34 of the balloon 30, each of the plurality of electrodes 18 being configured to record impedance signals from the area of tissue and deliver electroporation energy to the area of tissue; and an energy generator 14 in communication with the plurality of electrodes 18, the energy generator 14 having processing circuitry 50 configured to: receive impedance signals from the plurality of electrodes 18; identify at least one electrode 18 of the plurality of electrodes 18 that is in contact with the area of tissue based on impedance signals received from the plurality of electrodes 18; determine whether the plurality of electrodes 18 has uniform spacing when the balloon 30 is inflated based on impedance signals received from the plurality of electrodes 18; allow a delivery of electroporation energy to the plurality of electrodes 18 when the processing circuitry 50 determines the plurality of electrodes 18 has uniform spacing when the balloon 30 is inflated; and selectively deliver electroporation energy to the at least one electrode 18 of the plurality of electrodes 18 that the processing circuitry identifies as being in contact with the area of tissue.

In one aspect of the embodiment, the medical device 12 further includes a longitudinal axis 28, each of the plurality of electrodes 18 having a teardrop shape that is tapered in a proximal-to-distal direction, the plurality of electrodes 18 being radially arranged around the longitudinal axis 28.

In one aspect of the embodiment, the balloon 30 has a circumference, each of the plurality of electrodes 18 having a circular shape and the plurality of electrodes 18 being radially arranged around the circumference of the balloon 30.

In one aspect of the embodiment, the energy generator 14 is configured to deliver electroporation energy to the plurality of electrodes 18 in a plurality of energy delivery patterns.

In one aspect of the embodiment, the energy generator 14 is configured to deliver bipolar electroporation energy between adjacent pairs of the plurality of electrodes 18 to the area of tissue, the plurality of energy delivery patterns being a sequence of at least five energy delivery patterns.

In one aspect of the embodiment, the energy generator 14 is configured to deliver monopolar electroporation energy between at least one of the plurality of electrodes 18 and a supplemental electrode 18 located distal to the balloon 30.

In one embodiment, a method for electroporating tissue includes: positioning an expandable element 30 of a medical device 12 proximate an area of target tissue, the expandable element 30 including a plurality of electrodes 18, each of the plurality of electrodes 18 being configured to record impedance measurements; recording impedance measurements with each of the plurality of electrodes 18; transmitting the recorded impedance measurement to an energy generator 14; identifying, based on the recorded impedance measurements, at least one electrode 18 of the plurality of electrodes 18 that is in contact with the area of target tissue and that is a predetermined distance from at least one adjacent electrode 18 of the plurality of electrodes 18; and then delivering electroporation energy to the identified at least one electrode 18 in a sequence of energy delivery patterns by selectively one of activating and deactivating each of the at least one electrode 18 of the plurality of electrodes 18.

In one aspect of the embodiment, the method further includes delivering the sequence of energy delivery patterns such that there is a delay following each energy delivery pattern in the sequence of energy delivery patterns and each energy delivery pattern in the sequence of energy delivery patterns has a duration that is at least as long as a corresponding following delay.

In one embodiment, a medical system 10 includes: a medical device 12 configured to electroporate a targeted area of tissue, the medical device 12 including: an expandable element 30 having a plurality of splines 41, each of the plurality of splines 41 having a distal portion 41A and a proximal portion 41B, the plurality of splines 41 being transitionable between a linear first configuration and an expanded second configuration; and a plurality of electrodes 18 disposed on the distal portions 41A of the plurality of splines 41, each of the plurality of electrodes 18 being configured to record impedance signals from the targeted area of tissue and deliver electroporation energy to the targeted area of tissue; and an energy generator 14 in communication with the plurality of electrodes 18, the energy generator 14 having processing circuitry 50 configured to: deliver electroporation energy to the plurality of electrodes 18 in a sequence of a plurality of energy delivery patterns; and automatically switch between the plurality of energy delivery patterns of the sequence of the plurality of energy delivery patterns such that a pulse train of electroporation energy is delivered in each of the plurality of energy delivery patterns at least once when the system is in use.

In one aspect of the embodiment, the processing circuitry 50 is further configured to: receive impedance signals from the plurality of electrodes 18; identify at least one electrode 18 of the plurality of electrodes 18 that is located proximate the targeted area of tissue based on the impedance signals received from the plurality of electrodes 18; and selectively deliver electroporation energy to the at least one electrode 18 of the plurality of electrodes 18 that the processing circuitry 50 identifies as being located proximate the targeted area of tissue.

In one aspect of the embodiment, the processing circuitry 50 is further configured to: determine whether the plurality of electrodes 18 has uniform spacing when the plurality of splines 41 are in the expanded second configuration based on impedance signals received from the plurality of electrodes 18; and allow a delivery of electroporation energy to the plurality of electrodes 18 when the processing circuitry 50 determines the plurality of electrodes 18 has uniform spacing when the plurality of splines 41 are in the expanded second configuration.

As will be appreciated by one of skill in the art, certain concepts described herein may be embodied as a method, data processing system, and/or computer program product. Accordingly, these concepts described herein may take the form of an entirely hardware embodiment, an entirely software embodiment or an embodiment combining software and hardware aspects. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, the system comprising:
   a medical device configured to electroporate tissue, the medical device including a balloon having an equator, a distal portion, a proximal portion, and defining a longitudinal axis, the balloon having a plurality of electrodes, each of the plurality of electrodes having a teardrop shape with a wider proximal end and a narrower distal end that is tapered in a proximal-to-distal direction, the plurality of electrodes radially disposed on an exterior surface of the balloon on a plane transverse to the longitudinal axis with each wider proximal end disposed proximate the equator on the distal portion of the balloon and the narrower distal end disposed distal to the wider proximal end on the distal portion of the balloon; and
   an energy generator in communication with the plurality of electrodes, the energy generator having processing circuitry configured to:
   deliver electroporation energy to the plurality of electrodes;
   receive data from the plurality of electrodes;
   identify whether at least one electrode of the plurality of electrodes is in close proximity with, but not in contact with, an area of tissue based on the data received from the plurality of electrodes;
   determine whether an alert condition is present based on the data received from the plurality of electrodes, the alert condition being that the at least one electrode in close proximity with, but not in contact with, the area of tissue is not properly positioned; and
   at least one of cease a delivery of electroporation energy to the plurality of electrodes and prevent the delivery of electroporation energy to at least one electrode from the plurality of electrodes when the processing circuitry determines the alert condition is present.

2. The system of claim 1, wherein the data includes impedance measurements.

3. The system of claim 1, wherein the plurality of electrodes is configured to be uniformly spaced when the balloon is expanded.

4. The system of claim 3, wherein each of the plurality of electrodes is configured to record at least one impedance measurement, the processing circuitry being configured to receive the at least one impedance measurement from each of the plurality of electrodes and selectively activate at least one of the plurality of electrodes based on the at least one impedance measurement received from each of the plurality of electrodes.

5. The system of claim 1, wherein the system further includes a mapping system, the energy generator and processing circuitry being further configured to selectively connect each of the plurality of electrodes to the mapping system and record intracardiac electrogram signals from each of the plurality of electrodes.

6. The system of claim 1, wherein the medical device further includes at least one electrode distal to the balloon.

7. The system of claim 6, wherein the at least one electrode distal to the balloon is on a secondary medical device that is positionable distal to the medical device.

8. The system of claim 6, wherein the medical device further includes a distal tip that extends distally beyond the balloon, the at least one electrode distal to the balloon being on the distal tip.

9. The system of claim 1, wherein the energy generator is configured to deliver electroporation energy to the plurality of electrodes in a sequence of a plurality of energy delivery patterns.

10. The system of claim 9, wherein the processing circuitry is configured to automatically switch between the plurality of energy delivery patterns of the sequence of the plurality of energy delivery patterns such that a pulse train of electroporation energy is delivered in each of the plurality of energy delivery patterns at least once when the system is in use.

11. A medical system, the system comprising:
a medical device defining a longitudinal axis and being configured to electroporate an area of tissue, the medical device including:
a balloon having a distal portion a proximal portion, and an equator; and
a plurality of electrodes disposed on the distal portion of the balloon, each of the plurality of electrodes having a teardrop shape with a wider proximal end and a narrower distal end that is tapered in a proximal-to-distal direction, being radially disposed on an exterior surface of the balloon on a plane transverse to the longitudinal axis with each wider proximal end disposed proximate the equator on the distal portion of the balloon and the narrower distal end disposed distal to the wider proximal end on the distal portion of the balloon, the plurality of electrodes being configured to record impedance signals from the area of tissue and deliver electroporation energy to the area of tissue; and
an energy generator in communication with the plurality of electrodes, the energy generator having a processing circuitry configured to:
receive impedance signals from the plurality of electrodes;
identify whether at least one electrode of the plurality of electrodes is in close proximity with, but not in contact with, the area of tissue based on impedance signals received from the plurality of electrodes;
determine whether the plurality of electrodes has uniform spacing when the balloon is inflated based on impedance signals received from the plurality of electrodes;
allow a delivery of electroporation energy to the plurality of electrodes when the processing circuitry determines the plurality of electrodes has uniform spacing when the balloon is inflated; and
selectively deliver electroporation energy to at least one electrode of the plurality of electrodes that the processing circuitry identifies as being in contact with the area of tissue.

12. The system of claim 11, wherein the balloon has a circumference, each of the plurality of electrodes being radially arranged around the entire circumference of the balloon.

13. The system of claim 11, wherein the energy generator is configured to deliver electroporation energy to the plurality of electrodes in a plurality of energy delivery patterns.

14. The system of claim 13, wherein the energy generator is configured to deliver bipolar electroporation energy between adjacent pairs of the plurality of electrodes to the area of tissue, the plurality of energy delivery patterns being a sequence of at least five energy delivery patterns.

15. The system of claim 13, wherein the energy generator is configured to deliver monopolar electroporation energy between at least one electrode of the plurality of electrodes and a supplemental electrode located distal to the balloon.

* * * * *